US008470963B2

(12) United States Patent
Koltermann

(10) Patent No.: US 8,470,963 B2
(45) Date of Patent: Jun. 25, 2013

(54) MULTIFUNCTIONAL COMPOUNDS FOR PHARMACEUTICAL PURPOSES

(75) Inventor: Andre Koltermann, Icking (DE)

(73) Assignee: Sku Asset Management GmbH, Baiersbrunn (DE)

( * ) Notice: Subject to any disclaimer, the term of this patent is extended or adjusted under 35 U.S.C. 154(b) by 1064 days.

(21) Appl. No.: 12/305,898

(22) PCT Filed: Jul. 2, 2007

(86) PCT No.: PCT/EP2007/005836
§ 371 (c)(1),
(2), (4) Date: Dec. 19, 2008

(87) PCT Pub. No.: WO2008/000517
PCT Pub. Date: Jan. 3, 2008

(65) Prior Publication Data
US 2010/0233161 A1    Sep. 16, 2010

Related U.S. Application Data

(60) Provisional application No. 60/806,298, filed on Jun. 30, 2006.

(30) Foreign Application Priority Data

Jun. 30, 2006  (EP) ..................................... 06013640
Jun. 30, 2006  (EP) ..................................... 06013641

(51) Int. Cl.
*C07K 14/00* (2006.01)

(52) U.S. Cl.
USPC ........... 530/300; 530/326; 530/327; 530/328; 514/1.1

(58) Field of Classification Search
USPC .................... 530/300, 326, 327, 328; 514/1.1
See application file for complete search history.

(56) References Cited

U.S. PATENT DOCUMENTS

| 4,064,118 | A |   | 12/1977 | Wong |
| 4,427,660 | A |   | 1/1984 | Schiffmann et al. |
| 4,522,752 | A |   | 6/1985 | Sisto et al. |
| 5,580,563 | A | * | 12/1996 | Tam .......................... 424/197.11 |
| 7,524,821 | B2 | * | 4/2009 | Wang et al. ...................... 514/25 |
| 2003/0099629 | A1 |   | 5/2003 | Goldenberg et al. |
| 2004/0132640 | A1 | * | 7/2004 | DeFrees et al. .................... 514/8 |

FOREIGN PATENT DOCUMENTS

| EP | 1 398 322 | 3/2004 |
| EP | 1 398 327 | 3/2004 |
| EP | 1 398 328 | 3/2004 |
| WO | WO96/40749 | 12/1996 |
| WO | WO96/40772 | 12/1996 |
| WO | WO00/31261 | 6/2000 |
| WO | WO01/38342 | 5/2001 |
| WO | WO01/91780 | 12/2001 |
| WO | WO02/055543 | 7/2002 |
| WO | WO2004/024761 | 3/2004 |
| WO | WO2004/100997 | 11/2004 |
| WO | WO2004/101600 | 11/2004 |
| WO | WO2004/101606 | 11/2004 |
| WO | WO2004/101611 | 11/2004 |

OTHER PUBLICATIONS

Nishikawa (Methods in Enzymology 146, 11-22, 1987).*
Johnson, Dana J., Chemistry & Biology 4, 939-950, 1997.*
Rabiet et al.: "Human mitochondria-derived N-formylated peptides . . . ", in: Eur. J. Immunology, 2005, pp. 2486-2495.
Zonghai et al.: "Identification and characterization of a novel peptide . . . ", in: FASEB Hournal, Jan. 2005, pp. 1978-1985.
Obrist et al.: "Chemotactic monoclonal antibody conjugates . . . ", in: Biochemical and Biophysical research Communications, 1988, pp. 1139-1144.
Obrist et al.: "Monocyte chemotaxis mediated by . . . ", in: Int. J. Immunopharmacology, 1983, pp. 307-314.
Obrist et al.: "Enhancement of marcophage invasion of tumors . . . ", in: Cellular Immunology, 1983, pp. 169-174.
Hetland et al.: "Effect of formyl peptide-toxin conjugates on myeloid cancer . . . ", in: Int. J. Immunotherapy, 1995, pp. 85-93.
Pooyan et al.: "Conjugates bearing multiple formyl-methionyl peptides . . . ", in: Bioconjugate Chemistry, 2002, pp. 216-223.
Yao et al.: "Activation of formylpeptide receptor in human malignant glioma cells . . . ", in: Chinese Journal of Cancer, 2007, pp. 241-246.
Thierry et al.: "The synthetic peptide trp-lys-tyr-met-val-met-$NH_2$ specifically . . . ", in: J. Biological Chemistry, 2001, pp. 21585-21593.
Akiba et al.: "Extracellular production of human cystatin S . . . ", in: Protein Expression & Purification, 2006, pp. 203-210.
Avrutina et al.: "Fmoc assisted synthesis of a 29-residue . . . ", in: Europ. J. of organic Chemistry, 2004, pp. 4931-4935.
Chu et al.: "Synthesis of amplifiable reporter DNA for bioassays", in: Nucleic Acids Research, 1986, pp. 5591-5603.
Baskerville et al.: "A ribozyme that ligates RNA to protein", in: Nucleic Acids Research, 2002, pp. 9154-9159.
Blackburn et al.: "Solid-phase synthesis of . . . ", in: Method sin Enzymology, 1997, pp. 175-198.
Bycroft et al.: "Antibacterial and immunostimulatory properties . . . , in: Antimicrobal Agents and Rhemotherapy, 1989, pp. 1516-1521.
Caruthers et al.: "Chemical synthesis of . . . ", in: Methods in Enzymology, 1992, pp. 3-20.
Caruthers et al.: "Synthesis and biochemical studies ..", in: Ciba Found. Symp., 1991, pp. 158-166.
Chen et al.: "Temporin A and related frog . . . ", in: J. of Immunology, 2004, pp. 2652-2659.
Feranndez: "Prokaryotic expression of antibodies . . . ", in: Science Direct, Curr. Opin. Biotechnology, 2004, pp. 364-373.
Gobbo et al.: "Synthesis and biological activities . . . ", in: J. of Peptide research, 1997, pp. 336-341.
Hackeng et al.: "Chemical synthesis and spontaneous . . . ", in: PNAS, 2000, pp. 14074-14078.
Haribabu et al.: "Chemoattractant receptors activate . . . ", in: J. of Biological Chemistry, 1999, pp. 37087-37092.

(Continued)

*Primary Examiner* — David Lukton
(74) *Attorney, Agent, or Firm* — Henry M. Feiereisen LLC; Ursula B. Day, Esq.

(57) ABSTRACT

The invention relates to a synthetic bifunctional non-antibody compound comprising one or more effector moieties and one or more binder moieties, wherein the effector moieties are operably linked to the binder moieties via a linker, the effector moieties are ligands to at least one pathogen pattern recognition receptor (PRR) and the binder moieties bind to a marker of a tumor cell.

9 Claims, 1 Drawing Sheet

OTHER PUBLICATIONS

Harris: "Role of chemotaxis in inflammation", in: Phys. Review, 1954, pp. 529-562.
Lu et al.: "Crystal structure of human epidermal . . . ", in: J. of Biological Chemistry, 2001, pp. 34913-34917.
Hoare: "Procedure for the selective modification . . .", in: J. American Chemistry, 1966, p. 2057.
Ishida et al.: "peptides that contain unnatural . . . ", in: Reviews of Heteroatom Chemistry, 1999, pp. 79-142.
Eichler et al.: "Synthesis of cyclic disulfide peptides . . . ", in: Protein and Peptide Letters, 1997, pp. 157-164.
Jackson et al.: "Free radical induced polymerization . . . ", in: Vaccine, 1997, pp. 1697-1705.
James et al.: "Benzodiazepine Peptidomimetics . . . ", in: Science, 1993, pp. 1937-1942.
Kantchev et al.: "Direct Fmoc/tert-Bu solid phase . . . ", in: Bioplymers, 2006, pp. 232-240.
Koppitz et al.: "97. Synthesis of unnatural lipophilic . . .", in: Helvetic Chimica Acta, 1997, pp. 1280-1300.
Larsen et al.: "The Merrifield peptide synthesis . . .", in: J. Am. Chem. Soc, 1993, pp. 6247-6253.
Lew et al.: "A mannose receptor mediates . . . ", in: Am. Soc. For Clinical Investigation, 1994, pp. 1855-1863.
Lin et al.: "Solid-phase synthesis of . . . ", in: Bioorganic and Medicinal Letters, 1998, pp. 511-514.
Papas et al.: "Gene amplification and analysis", vol. 3, 1983, pp. 1-26.
Merrifield: "Solid phase peptide synthesis . . . ", in: J. Am. Chem. Soc, 1963, p. 2149.
Migeotte et al.: "Identification and characterization . . . ", in: J. of Experimental Medicine, 2005, pp. 83-93.
Mills et al.: "Identification of a ligand binding site . . . ", in: J. of Biological Chemistry, 1998, pp. 10428-10435.
Murphy et al.: "The formyl peptide chemoattractant . . . ", in: Fed. of European Biochemical Societies, 1990, pp. 353-357.
Mytar et al.: "Induction of intracellular cytokine production . . . ", in: Inflammation Research, 2004, pp. 100-106.
O'Donnell et al.: "Solid-phase synthesis of unnatural . . . ", in: Tetrahedron Letters, 1997, pp. 7163-7166.
O'Donnell et al.: "Solid-phase unnatural peptide synthesis", in: J. Am. Chem. Soc., 1996, pp. 6070-6071.
Oostendorp et al.: "An immunosuppressive retrovirus-derived . . . ", in: J. of Immunology, 1992, pp. 1010-1015.
Oostendorp et al.: "Synthetic hexapeptides derived from . . . ", in: J. of Leukocyte Biology, 1992, pp. 282-288.
Oostendorp et al.: "Suppression of lymphocyte proliferation . . . ", in: European J. of Immunology, 1992, pp. 1505-1511.
Peng et al.: "Combinatorial chemistry identifies . . . ", in: Nature Chemical Biology, 2006, pp. 381-389.
Perez et al.: "Cloning of Gene Coding . . . ", in: Biochemistry, 1992, pp. 11595-11599.
Roberts et al.: "Chemistry for peptide and protein PEGylation", in: Advanced Drug Delivery Reviews, 2002, pp. 459-476.
Schiffmann ert al.: "The isolation and partial characterization . . . ", in: J. of Immunology, 1975, pp. 1831-1837.
Schiffmann et al.: "N-formylmethionyl peptides . . . ", in: Proc. Nat. Acad. Sci USA, 1975, pp. 1059-1062.
Schmoldt et al.: "A fusion protein system for the . . . ", in: Protein Expression & Purification, 2004, pp. 82-89.
Scott et al.: "The solid phase synthesis of . . . ", in: Tetrahedron letters, 1997, pp. 3695-3698.
Sheridan et al.: "Solid-phase synthesis and . . . ", in: J. of Peptide Science, 1999, pp. 555-562.
Smith et al.: "The imidazoquinolines and their . . . ", in: Pharmacother., 2003, pp. 1105-1119.
Smith et al.: "Solid-phase peptide synthesis . . . ", in: Int. J. Peptide Protein Res., 1994, pp. 183-191.
Spector et al.: "Expression of N-formylated proteins . . . ", in: Protein Expression & Purification, 2003, pp. 317-322.
Takano et al.: "Aspirin-triggered 15-Epi-Lipoxin . . . ", in: J. Exp. Med., 1997, pp. 1693-1704.
Tam et al.: "A biomimetic strategy in the synthesis . . . ", in: Protein Science, 1998, pp. 1583-1692.
Tam et al.: "Synthetic peptide vaccine design: Synthesis . . . ", in: Proc. Natl. Acad. Sci. USA, 1988, pp. 5409-5413.
Trill et al.: "Production of monoclonal antibodies . . . ", in: Curr. Opin. Biotechnology, 2004, pp. 553-560.
Ulbrich et al.: Polymeric drugs based on conjugates . . . , in: J. of Controlled release, 2000, pp. 63-79.
Wei-Dong Jia et al.: "A noven peptide that selectively . . . ", in: Cancer Letters, 2007, pp. 234-242.
Wrighton et al.: "Increased potency of an erythropoietin peptide . . .", in: Nature Biotechnology, 1997, pp. 1261-1265.
De Yang et al.: "Human dendritic cells express . . . ", in: J. of Leukocyte Biology, 2002, pp. 598-607.
Zhang et al: "Synthesis and application of unprotected . . .", in: J. Am. Chem. Soc., 1997, pp. 2363-2370.

* cited by examiner

MULTIFUNCTIONAL COMPOUNDS FOR PHARMACEUTICAL PURPOSES

CROSS-REFERENCES TO RELATED APPLICATIONS

This application is a national stage entry of PCT/EP07/05836, filed Jul. 2, 2007, which claims priority to provisional application 60/806,298, filed Jun. 30, 2006, and foreign priority to both EP06013640.5, filed Jun. 30, 2006 and EP06013641.3, filed Jun. 30, 2006.

BACKGROUND OF THE INVENTION

The invention relates to novel multifunctional compounds for the use in treating diseases in patients in the need thereof.

The immune system has the ability to specifically or unspecifically respond to antigens (including self antigens and foreign antigens). However, in certain cases the immune system fails to recognize and to respond to these structures, such as pathogens, e.g. foreign pathogenic cells, cancer cells, or infectious agents. In other cases an immunological response is not sufficiently localized to a certain tissue or organ and thus may cause severe adverse side effects within the patients.

Consequently, it is an objective of the present invention to provide novel compounds which are capable of inducing and targeting of an immunological response to a specific predetermined medicinal target within the patient. Furthermore, it is the objective of the present invention to provide novel multifunctional compounds, which enable an effective targeting of a biologically active structure to a tumor cell.

SUMMARY OF THE INVENTION

This objective is accomplished by a compound according to the invention which comprises at least one binder which is operably linked to at least one effector. The effector is any substance which induces, controls, mediates or is otherwise involved in an immunological response of the host. In particular, the effector induces the immunological response, in particular of the innate immune system.

The term "effector" refers to any molecular structure, which induces, modulates, controls or is otherwise involved in the innate or acquired immune system within the host. In particular, the effector exhibits chemical properties that are involved in the migration of cells (chemotaxis) of the innate immune system and/or their activation. Accordingly, the effectors of the present invention can be chemoattractants for immunological cells and/or immunostimulants for the innate or acquired immune system within the host. Since they can also activate or enhance the immune system, they can furthermore exhibit properties of an adjuvant. In particular, the effectors of the invention can be involved in mediating cell mediated cytotoxicity. One important function of the effector can be the involvement of the antibody induced cellular cytotoxicity (ADCC).

The immunological response induced or modulated by the compound of the invention can be any kind of response exhibited by the host by any element or compound of the immune system. Elements of the immune system include chemical compounds and cells which are involved in the acquired or innate immune system. Typical compounds of the immune system are cytokines, such as interleukin, TNF or interferon or antibodies. Typical immunological cells are leucocytes, e.g. lymphocytes, such as T- and C-cells, macrophages or neutrophils or dendritic cells.

It can be advantageous to select an agonist of a PRR (pathogen recognizing receptor) as an effector. In a certain embodiment of the invention the novel multifunctional compound can comprise at least two effectors, wherein one effector can be an immunostimulants and the other effector can be the Fc Fc domain of an antibody.

An effector can comprise a pathogen-associated molecular pattern (PAMPS), which is recognizable by a PRR and activates the PRR to exhibit at least one of its biological functions within the innate immune system.

PRRs are receptors of the innate immune system. The innate immune system represents a defense mechanism that a host uses immediately or within several hours after exposure to an antigen which is non-specific to such antigen. Unlike adaptive immunity, innate immunity does not recognize every possible antigen. Instead, it is designed to recognize a few highly conserved structures present in many different pathogens. The structures recognized are pathogen-associated molecular patterns and e.g. include LPS from the gram-negative cell wall, peptidoglycan, lipoteichoic acids from the gram-positive cell wall, the sugar mannose (common in microbial glycolipids and glycoproteins but rare in those of humans), fucose, N-acetyl glucosamine, bacterial DNA, N-formylmethionine found in bacterial proteins, double-stranded RNA from viruses, and glucans from fungal cell walls.

Most body defense cells have pattern-recognition receptors for these common pathogen-associated molecular patterns. Consequently, there is an immediate response against the invading pathogen. Pathogen-associated molecular patterns can also be recognized by a series of soluble pattern-recognition receptors in the blood that function as opsonins and initiate the complement pathways. Taken together, the innate immune system is thought to recognize approximately $10^3$ molecular patterns.

As defined hereinafter PRRs of the invention comprise either surface PRRs or soluble PRRs. The cell surface PRRs can be subdivided into two functionally different classes: endocytic pattern-recognition receptors and signaling pattern-recognition receptors. Endocytic pattern-recognition receptors are found on the surface of immune cells and promote the attachment of pathogens to phagocytes and their subsequent engulfment and destruction.

The targeted PRRs of the invention include inter alia mannose receptors (MR), formyl peptide receptors (FPRs), toll-like receptors (TLRs), CD14, and nucleotide-binding oligomerization domain proteins (NOD). Binding of ligands to these receptors also promotes the synthesis and secretion of intracellular regulatory molecules (immune modulating signals) such as cytokines that are crucial to initiating innate immunity and adaptive immunity.

Endocytic PRRs include mannose receptors (MR), which bind to terminal mannose and fucose groups of glycoproteins and glycolipids (human glycoproteins and glycolipids typically have terminal N-acetylglucosamine and sialic acid groups), whereas scavenger receptors represent another type of endocytic PRRs, and bind to bacterial cell wall components such as e.g. LPS, peptidoglycan and teichoic acids. There are also scavenger receptors for certain components of other types of microorganisms.

MRs are found e.g. on the surface of dendritic cells and are endocytic and phagocytic receptors belonging to the C-type lectin superfamily. A number of functions have been ascribed to this receptor, which is involved in innate and adaptive immune responses. MR are specifically responsible for endocytic capture of pathogens in early stages of immune response. The MR binds carbohydrate moieties on several pathogens, such as bacteria, fungi, parasites, and viruses, and, therefore, is considered a pattern recognition receptor (PRR). In addition, MR binds endogenous molecules and was originally described as a membrane-associated component binding lysosomal glycosidases in alveolar macrophages. Since its identification, many other endogenous ligands were described, including hormones, enzymes, cell membranes, extracellular matrix components, and normal as well as tumoral mucins. The MR is preferentially expressed on immune cells of myeloid lineage, especially subsets of dendritic cells (DC) and tissue macrophages. In addition to immune cells, specialized endothelial cells are also MR-positive.

TLRs play a major role in innate immunity and the induction of adaptive immunity. Different combinations of TLRs appear in different cell types and may appear in pairs. For example: TLR-1/TLR-2 pairs bind uniquely bacterial lipopeptides and glycosylphosphatidylinositol (GPI)-anchored proteins in parasites; TLR-2/TL6 pairs bind lipoteichoic acid from gram-positive cell walls and zymosan from fungi; TLR-2 plays a role in binding peptidoglycan fragments (glycopeptides) or TLR-4/TLR-4 pairs bind lipopolysaccharide from gram-negative cell walls. With the activation of TLRs by binding of a ligand the TLR transmits a signal to the cell's nucleus inducing the expression of genes coding for the synthesis of intracellular regulatory molecules called cytokines (e.g. TNF-alpha or interleukin). The cytokines, in turn, bind to cytokine receptors on other defense cells.

CD14 is found on monocytes, macrophages, and neutrophils and promotes the ability of TLR-4 to respond to LPS and peptidoglycan. Interaction of these molecules with CD14 and TLR-4 leads to an elevated synthesis and secretion of proinflammatory cytokines such as IL-1, IL-6, IL-8, TNF-alpha, and PAF. These cytokines then bind to cytokine receptors on target cells and initiate inflammation and activate both the complement pathways and the coagulation pathway.

NOD (nucleotide-binding oligomerization domain) proteins, including NOD1 and NOD2, are cytosolic proteins that allow intracellular recognition of peptidoglycan components. NOD1 recognizes peptidoglycan containing the muramyl dipeptide NAG-NAM-gamma-D-glutamyl-meso diaminopimelic acid, part of the peptidoglycan monomer in common gram-negative bacteria and just a few gram-positive bacteria. NOD2 recognizes peptidoglycan containing the muramyl dipeptide NAG-NAM-L-alanyl-isoglutamine found in practically all bacteria.

As macrophages phagocytose either whole bacteria or peptidoglycan fragments released during bacterial growth, the peptidoglycan is broken down into muramyl dipeptides. Binding of the muramyl dipeptides to NOD1 or NOD2 leads to the activation of genes coding for proinflammatory cytokines in a manner similar to the cell surface toll-like receptors.

Formyl Peptide Receptors

In a particularly preferred embodiment of the invention the binder is operably linked to an effector, which activates a formyl peptide receptor (FPR). This group of receptors also belongs to the class of signaling PRR. FPRs are G-protein coupled receptors expressed primarily in neutrophils and some cells of macrophage or phagocyte lineage. The best-characterized ligands for these receptors are peptides or protein fragments containing N-formyl methionine residues, a hallmark of proteins of prokaryotic origin. As such, these peptides serve as potent immunological homing signals for sites of bacterial infection, signaling several phases of neutrophil response and activation, including chemoattraction, stimulation of production and release of immunosignaling molecules (e.g., interleukins, cytokines, etc.), as well as degranulation, a cellular process that includes the production and release of both chemical (e.g., hydrogen peroxide and other reactive oxygen radical species) and enzymatic agents (e.g., elastase and other digestive enzymes) capable of mediating destruction of the foreign agent or pathogen.

In humans, three related FPR family members have been identified: the eponymous formyl peptide receptor (FPR), as well as two other receptors, FPRL1 and FPRL2. FPRL1 and FPRL2 are related to FPR by sequence homology but appear to be functionally distinct. Lipoxin A4 and serum amyloid A (SAA) have been proposed as natural ligand for FPRL1R (Takano et al., J. Exp. Med. 185:1693-1704 (1997)). A naturally occurring ligand for FPR is formyl-methionine-leucine-phenylalanine (fMLF).

The cellular response mediated by the formyl peptide receptor (FPR) includes cellular polarization and transmigration, generation of superoxide O2 radicals through respiratory burst oxidase, degranulation and release of a variety of various degradative enzymes, as well as phagocytosis. According to the invention the effector interacts with the FPR and therewith induces at least one of the above mentioned cellular responses.

In addition to the cell surface pattern-recognition receptors the multifunctional compounds of the invention can comprise at least one binder, which functionally interacts with a secreted pattern-recognition receptor. These soluble PRRs bind to pathogens and enable them to be recognized by the complement pathways and phagocytes. For example, mannan-binding lectin is synthesized by the liver and released into the bloodstream where it can bind to the carbohydrates on bacteria, yeast, some viruses, and some parasites. This, in turn, activates the lectin complement pathway and results in the production of C3b, a molecule that promotes the attachment of microorganisms to phagocytes.

Definitions

The term pattern recognition receptors (PRRs) as used in the present invention refers to a class of proteins expressed by cells of the immune system. PRRs are activated by pathogen-associated molecular patterns (PAMPs). Pathogen pattern recognition receptors (PRRs) generally recognize common structural and molecular motifs as e.g. present on pathogenic surfaces or evolving during the degradation of pathogens or mitochondria and contribute to induction of the innate immune responses. E.g. the MR is considered one such PRR as is the FPR and TLR.

"Pathogen-associated molecular patterns" (PAMPs) are small molecular sequences consistently found on pathogens or evolving during the degradation of pathogens or mitochondria. They are recognized by PRRs, such as TLR or FPR or MR. Lipopolysaccharide (LPS) is considered to be the pro-typical PAMP. Other PAMPs include lipoteichoic acid from gram positive bacteria, peptidoglycan, and nucleic acid variants normally associated with viruses, such as double-stranded RNA (dsRNA) (for more examples see below).

The term "pathogen" preferably refers to any organism, cell or structure that is capable of being harmful to the host or desired to be eliminated in the host. Examples for pathogens are bacteria, viruses, fungi, parasites, tumor cells. In the sense of the present invention also structures desired to be eliminated for cosmetical or other reason are understood as pathogens.

The term "binder" as used in the present invention preferably refers to any molecular structure, which interacts/binds with a second molecular structure. The term "second molecular structure" refers to any structure which is capable of distinguishing host structures from targets either quantitatively or qualitatively, as e.g. in the case of overexpressed tumor markers that are also present on host cells, but in lower quantity. The interactions between the first and second molecular structure can comprise any kind of chemical or physical interaction, including covalent and non-covalent bonds, e.g. hydrogen bonds, van-der-Wals forces or hydrophobic interactions. Preferred example are given in table 1.

Selectively binding to cancer or tumor cells means forming a complex with a cancer cell or a marker on the surface of a cancer cell at a statistical frequency higher than forming a complex with a typical non-cancer cell as assayed with typical binding assays such as immunostaining, ELISA, gel-shift assays, Biacore or similar methods.

The second molecular structure preferably is a marker. A "marker" can be any structure, which is sufficiently specific for a distinct physiological or pathological function, or pathogen, therewith enabling its identification and/or its discrimination from other host structures. The specificity of the marker can be due either to its selective expression or its enhanced expression in or on or at the proximity of said structure or cellular unit. Thus, the term specificity comprises qualitative and/or quantitative aspects.

Most preferred the marker is specific for a distinct cellular unit, e.g. a tumor cell-surface antigen, a stromal component of a tumor, an intracellular antigen or a intracellular antigen. The term "cellular unit" refers to any cellular structure comprising cells, cell types, cell assemblies or tissues and parts thereof.

The binder of the invention can be of natural or synthetic origin and be modified or unmodified. Binders of the present invention include small molecules, biological polymers or oligomers, such as e.g. proteins, peptides, microproteins and mimetics, peptide mimetics, modified or unmodified amino acids or polynucleotides and oligonucleotides, including RNAi, as well as fragments, derivatives, analogs, chimerics or polymers of the aforementioned.

Other examples of binders include synthetically produced small molecules. The term "small molecule" preferably refers to a bioactive molecule with preferably a molecular weight of below 500 Da. Small molecules are molecules other than peptides, proteins, DNA or RNA.

The second molecular structure functionally can be a medicinal target. The term "medicinal target" refers to any molecular or cellular structure with the—actual or at least assumed—potential to suit as a working or starting point for a drug or drug candidate in order to diagnose, prevent, mitigate or treat a disease of the host, preferably a human patient. Examples for target molecules are receptors, enzymes and ion channels. Numerous of such target molecules with proven pharmacological relevance are known in the art. Examples are given in table 2.

The term "effector" preferably refers to any molecular structure, which induces, controls or otherwise is part of an immunological response, of either the acquired/adaptive or the innate immune system. The effectors of the present invention include small molecules, saccharides or polysaccharides, biological polymers or oligomers, such as e.g. proteins, peptides, microproteins and mimetics, peptide mimetics, modified or unmodified amino acids or polynucleotides and oligonucleotides as well as fragments, derivatives, analogs, chimerics or polymers thereof. Effector molecules are capable of binding to a receptor, though not necessarily at the binding site of the natural ligand. Effectors can modulate signal transduction when used alone, i.e., can be surrogate ligands, or can alter signal transduction in the presence of the natural Ligand.

The term effector also comprises compounds and mixtures thereof which increase or enhance the immunological of the host. Such compounds are usually defined as adjuvants. In particular, adjuvants enhance the production of antibodies against an antigen within the host.

In a preferred embodiment of the invention, the effectors comprise any molecular structure which is distinct from self-antigens of the host, which preferably is a mammal. Hence, the effectors of the present invention can be non-mammalian structures, e.g. proteins/peptides as well as nucleotides and carbohydrates derived from bacteria and virus or synthetic origin as well as fragments, derivates or modifications thereof, which are not present in the healthy mammals. Possible effectors include lipopolysaccharides and teichoic acids shared by all gram-negative and gram-positive bacteria, unmethylated CpG motifs characterized by bacterial but not mammalian DNA, double-stranded RNA as a structural signature of RNA viruses, and mannans which are conserved elements of yeast cell walls. Other examples are formyl peptides. One important function of the effectors can be the immune cell activation.

Effectors are preferably agonist of PRR, i.e. they induce or otherwise enhance the signal transduction activity of the receptor.

Effectors especially include synthetic small molecules with stimulatory, modifying or activating effects on the innate immune system, such as imidazoquinoline compounds (cf. Smith et al Pharmacother. 2003 July; 4(7):1105-19). The effectors of the invention can be naturally derived but are preferably synthetically produced. Recombinant technology is considered to be a way of synthetic manufacture.

As used in the present invention the term "innate immune system" preferably refers to non-adaptive immunity of an organism. The elements of the innate immunity are generally able to distinguish foreign antigens (pathogens) from self antigens. Hence, the innate immune response does not adapt to a particular antigen and will remain unchanged even after repeated exposures to it. In contrary, the adaptive (or acquired) immune system improves its effectiveness against previously encountered antigens. Elements of the innate immunity are e.g. phagocytic cells (neutrophils, monocytes, and macrophages), cells that release inflammatory mediators (basophils, mast cells, and eosinophils), natural killer cells (NK cells), dendritic cells (DC) and molecules such as complement proteins, acute phase proteins, and cytokines.

The most important compounds of the innate immune system are chemicals such as lysozymes and chemoattractants (e.g. cytokines or histamine), or complement proteins. The most relevant cells of the innate immune system include macrophages, neutrophils including polymorphonuclear neutrophils, lymphocytes and NK cells. These cells are effective in destroying and removing pathogens as well as diseased tissues or cells.

The term "linker" preferably refers to any structures which operably links at least one effector and one binder. As used herein, "operably linked" means that under physiological conditions of pH, ionic strength and osmotic potential, the majority of the entities of the effector and the binder are associated with each other and both entities can exhibit their intended function.

If the linker covalently binds the effector and the binder, its minimum length is one covalent bond, e.g. one peptide bond. Other linkers comprise a variety of chemical linking and crosslinking agents including, for example, homo- or hetero-multifunctional, oligo- or heterofunctional crosslinking agents. Linking or crosslinking can be achieved by any of a variety of chemistries well known in the art including, for example, activated polyethylene glycols, aldehydes, isocyanates, maleimides and the like.

The term "activation" when used in combination with cells or receptors (and quantitative measurement or qualitative assessment thereof) preferably refers to any direct or indirect immune response, including, for example, infiltration, degranulation, rolling, chemotaxis, phagocytosis, endocytosis, increased expression or activity of various catabolic or degradative enzymes (e.g., elastases), oxidative burst, production or release of hydrogen peroxide and other highly reactive oxygen species, intracellular calcium flux, cell polarization, and changes in inositol metabolism and signaling. Other determinants of activation include increased expression and production of leukotrienes, complement, chemokines, cytokines, chemoattractant factors, interleukins, or interferons.

Methods for measuring these activities are well known to those skilled in the art. (See e.g., William E. Paul, Fundamental Immunology, Lippincott Williams and Wilking Publishers. 1999; John E. Coligen et al., Current Protocols in Immunology, John Wiley & Sons, New York, N.Y., 1999.)

The terms "mimetope" and "peptidomimetic" are used interchangeably herein. A "mimetope" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) Science 260: 1937-1942) and "retro-inverso" peptides (see U.S. Pat. No. 4,522,752 to Sisto). The terms "mimetope" and "peptidomimetic" also refer to a moiety, other than a naturally occurring amino acid, that conformationally and functionally serves as a substitute for a particular amino acid in a peptide-containing compound without adversely interfering to a significant extent with the function of the peptide (e.g., FPRL-1 agonists).

Examples of amino acid mimetics include D-amino acids. Peptides substituted with one or more D-amino acids may be made using well known peptide synthesis procedures. Additional substitutions include amino acid analogs having variant side chains with functional groups, for example, b-cyanoalanine, canavanine, djenkolic acid, norleucine, 3phosphoserine, homoserine, dihydroxyphenylalanine, 5-hydroxytryptophan, 1 methylhistidine, or 3-methylhistidine.

As used herein an "analog" of a compound X preferably refers to a compound which retains chemical structures of X necessary for functional activity of X, yet which also contains certain chemical structures which differ from X. An example of an analog of a naturally-occurring peptide is a peptide which includes one or more non-naturally occurring amino acids. The term "analog" is also intended to include modified mimetopes and/or peptidomimetics, modified peptides and polypeptides, and allelic variants of peptides and polypeptides. Analogs of a peptide will therefore produce a peptide analog that is substantially homologous to the original peptide.

The term "substantially homologous", when used in connection with amino acid sequences, preferably refers to sequences which are substantially identical to or similar in sequence, giving rise to a homology in conformation and thus to similar biological activity. The term is not intended to imply a common evolution of the sequences.

Typically "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

Generally, to determine the percent homology of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first amino acid sequence which has for example 100 amino acid residues, at least 30, preferably at least 40, more preferably at least 50, even more preferably at least 60, and even more preferably at least 70, 80 or 90 amino acid residues are aligned).

As used herein, "cell surface receptor" preferably refers to molecules that occur on the surface of cells, interact with the extracellular environment. Such molecules often transmit or transduce the information regarding the environment intracellularly in a manner that ultimately modulates transcription of specific promoters, resulting in transcription of specific genes.

The term "microproteins" preferably refers to small size proteins, which are preferably highly stable and resistant to heat, pH, and proteolytic degradation. Typically they have less than 50 amino acids. They have a defined structure based on the intra-molecular disulfide bonds.

The term ADCC (antibody-dependent cell-mediated cytotoxicity) as use herein refers to an immune response in which antibodies, by coating target cells, makes them vulnerable to attack by immune cells. Today, it is more and more understood that mediating cellular toxicity by ADCC is the important step in many of the different therapies with monoclonal antibodies.

The term antibody comprises any immunoglobulin or parts and fragments thereof, which are involve in the identification and neutralization of a foreign antigen. An antibody recognizes a specific antigen unique to its target. The Fc fragment of the antibody plays an important role in ADCC, since the Fc fragment is recognized by immunological cells. This, on one embodiment of the invention the effector of the multifunctional compound comprises an Fc fragment.

The term "preferably" is meant to suggest alternatives to the invention and not to limit or restrict the invention in any way

DETAILED DESCRIPTION OF THE INVENTION

Figure 1:
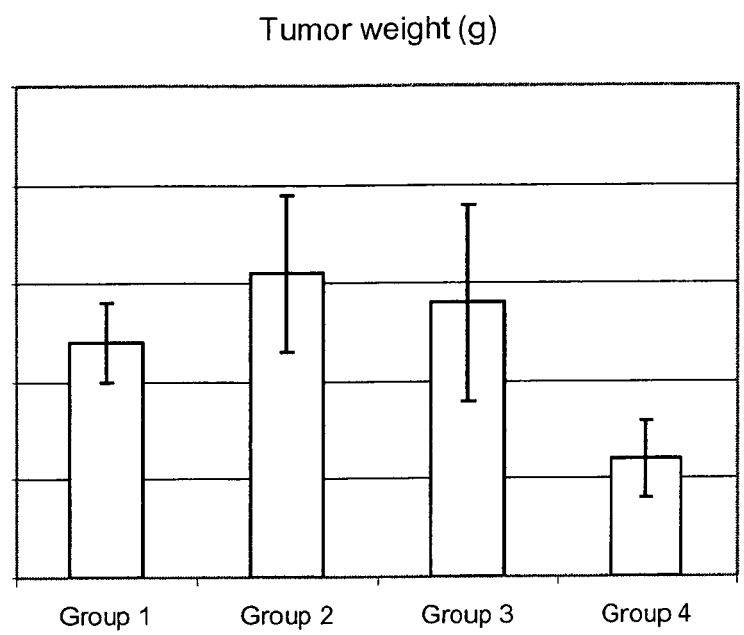
FIG. 1 shows the mean tumor weight which is significantly decreased in animals from Group 4 (injected with compound, see Example III) compared to control group 1 (PBS). Group 2 (binder only) and 3 (effector only) show no or only marginal effect on tumor size.

As outlined above, the multifunctional compounds of the invention comprise at least one binder and at least one effector.

Examples for effectors of the present invention are oligo- and polypeptides, peptides (modified, synthetic or natural), formylated peptides, in particular fM peptides, peptidoglycans from bacterial cell walls, prokaryotic cells, prokaryotic cell lysates, or lysates from eukaryotic cells containing mitochondrially derived N-formyl peptides, acylated lipopeptides, e.g. diacylated mycoplasmal lipopeptides or triacylated bacterial lipopeptide and tryacyl lipopeptide (Pam3CSSNA), diaminopimelic acid containing desmuramyl peptide (gamma-D-glutamyl-meso-DAP; iE-DAP), and muramyl-dipeptide (MDP), proteins from bacteria, agglutinates/adhesines from bacteria, e.g. Fimbrial subunit (CsgA) from *S. typhimurium* or Fimbriae (from *Porphyromonas gingivalis*), which function as a surface adhesion, flagellin from bacterial, N-acetylated elongation factors from bacteria, e.g. Tu (EF-Tu) from *E. coli*, outer membrane proteins from bacteria, e.g. *K. pneumoniae* (KpOmpA), proteins from antibodies, Fc-part of an antibody, proteins from antigens, antigens from neutralizing antibodies, antigens inducing the complement cascade, oligonucleotides, CpG containing DNA from bacteria, dsRNA of viruses, oligo- or polycarbohydrates, mannose containing oligo- or polycarbohydrates, mannan and/or mannose residues (fucose) from yeast and bacterial cell walls, lacto-N-fucopentaose III (LNFPIII) from helminths, modified oligo- or polycarbohydrates, LPS from bacteria, glycolipid like molecule on pathogens, Imidazoquinolines, phosphocholine.

Other examples of effectors according to the invention are compounds from the adaptive (acquired) immune system. These examples comprise antibodies and fragments thereof, in particular the Fc-part of an antibody and proteins or peptides, which are homologous thereto, proteins or peptides, that bind to the Fc-gamma receptor, peptide mimetics that binds to the Fc-gamma receptor, small molecule that binds to the Fc-gamma receptor and antigens that promote an adaptive immune response.

In a preferred aspect of the invention the novel compounds comprise an effector which induces or supports ADCC. Preferably, the effector binds to the Fc receptors (FcγRs) on the surface of immune effector cells such as natural killer cells or macrophages, leading to the phagocytosis or lysis of the targeted cells.

Preferably effectors are used which modulate the activity of FPR and analogs thereof. These ligands preferably are agonist of formyl peptide receptor like-1 (FPRL-1). In one embodiment of the invention, the polypeptide comprises from 1 to 80 amino acid residues, more preferably from 3 to 40 amino acid residues, more preferably from 3 to 20 amino acid residues, and still more preferably from 3 to 13 amino acid residues. In general, the EC50 values for the ligand agonists range from about $2\times10^{-9}$M to about $20\times10^{-6}$M. Preferably, the ligand agonist has an EC50 of $2\times10^{-6}$ M or less. In a preferred embodiment, the ligand agonist has an EC50 of $3\times10^{-6}$M. In one embodiment, the EC50 of the ligand agonist is determined by a calcium mobilization assay known to the one skilled in the art.

A particularly preferred effector of the group of formylmethionyl-peptide is formyl-methionylleucylphenylalanine (fMLP). FMLP is a proinflammatory peptide which is able to stimulate many leukocyte functions. It stimulates neutrophil chemotaxis, lysosomal enzyme release, oxygen-free radical production, Ca++ flux, leukotriene release by neutrophils and smooth muscle contraction. fMLP stimulation of neutrophils induces rapid alterations in their expression of adhesion receptors. In addition, fMLP has been shown to induce superoxide production and an increase in intracellular Ca++ levels. FIMLP has been shown to induce chemotaxis in a number of cells, including pulmonary alveolar macrophages, neutrophils, dendritic cells (DC) and monocytes. In fact, the chemotactic or chemoattractant activity of fIMLP is sufficiently well established that fMLP is often used as a positive control in chemotactic assays.

In the 1950s, it was observed that extracts of tissues infected with viable bacteria contain neutrophil and macrophage attractants (Harris, Physiol. Rev. 34:529-562 (1954)). These factors were later discovered to be N-formylmethionyl peptides which are present in filtrates of both gram-positive and gram-negative bacteria (Schiffmann et al., Proc. Natl. Acad. Sci. USA 72:1059-1062 (1975); Schiffmann et al., J. Immunol. 114:1831-18 (1975)). Immune response to bacterial pathogens results in the release of degraded peptides containing formylated methionine, that serve as highly potent chemoattractants for leukocyte and macrophage migration and infiltration. The receptor for these peptides has been cloned (Murphy et al., FEBS Lett. 261:353-357 (1990); Perez et al., Biochemistry 31:11595-11599 (1992)) and identified as a seven transmembrane G protein coupled receptor (GPCR). The cellular response mediated by binding of formylated peptide antagonists to the formyl peptide receptor (FPR) includes cellular polarization and transmigration, generation of superoxide O2<-> radicals through respiratory burst oxidase, degranulation and release of a variety of various degradative enzymes, as well as phagocytosis.

As outlined above, FPR receptors are surface receptors expressed on myeloid cells, namely phagocytes (monocytes (e.g. dendritic cells and macrophages) as well as granulocytes. Neutrophils—as the most abundant subset of granulocytes—thus play a crucial role in defense against infection. They are among the first cells that migrate to sites of infection to eliminate foreign bodies from those sites. They are abundant in the blood, but absent from normal tissue. Upon chemotactic recruitment to a site of infection and activation through various signaling molecule gradients that stimulate cellular receptors at nanomolar concentrations (i.e., chemoattractants, interleukins, and chemokines), neutrophils initiate a cascading cellular and physiological response, ultimately resulting in the release of superoxide and elastase, the release of other factors that further amplify the immune response, recruitment of monocytes, and phagocytosis of the antigenic body. These events represent important physiological components of innate immune response.

Accordingly, it is one object of the present invention to provide a multifunctional compound, which comprises an effector molecule, which induces direct and/or indirect the activation of neutrophils by a signal transduction via FPR binding, preferably by linking a formylmethionyl-peptide, in particular, formyl-methionylleucylphenylalanine (fMLP) to a suitable binder (see below). In this embodiment, thus, the multifunctional compound of the invention binds to a cell surface receptor of neutrophils and monocytes.

According to a further aspect of the invention the multifunctional compound comprises an effector which interacts with the mannosyl fucosyl receptor (MFR). The MFR is a 180-kDa $Ca^{2+}$-dependent lectin that functions as an endocytic receptor. It was first isolated from macrophages, but it has been found on a variety of other cells types, including dendritic cells, hepatic endothelial cells, retinal pigment epithelial cells, and kidney mesangial cells. The receptor consists of 10 extracellular domains followed by a transmembrane region and short cytoplasmic tail. The extracellular domains are the amino-terminal cysteine-rich domain, a fibronectin type II repeat domain, and eight tandem carbohydrate recognition domains. The carbohydrate recognition domains bind accessible mannose, fucose, and N-acetylglucosamine residues but have a higher affinity for complex ligands with multiple binding sites, such as mannan on yeast surface.

In another aspect of the invention the novel compounds comprise at least two effectors, whereas one can induce an immunological response of the innate immune system and a second effector induces a response of the adaptive immune system. In a particularly preferred embodiment of the invention the compound can comprise a ligand of a PRR (e.g. for FPR) and one ligand of the Fc receptor.

It is a further object of the present invention to provide a multifunctional compound, which comprises an effector molecule, which induces direct and/or indirect the activation of dendritic cells by a signal transduction via MR or FPRL2 binding, preferably by linking a D-Methionine or mannose molecule, to a suitable binder (see below). In this embodiment, thus, the multifunctional compound of the invention binds to a cell surface receptor of dendritic cells.

Examples of binders according to the invention are synthetic or natural peptides (linear, cyclic or branched), peptide mimetic, microproteins, peptide repeats, polypeptide structure comprising peptide sequence, microproteins (e.g. cystein knots, etc), immunoglobulin and fragments thereof (scFvs, Fab, domains, etc), oligonucleotides (e.g. DNA oligonucleotide (aptamers), RNA oligonucleotide (e.g. aptamers), oligonucleotide analogs (PNA, DNA/RNA chimera, etc.) or small molecules.

The binders should be capable of preferentially targeting pathogens in the host animal as e.g. bacterial cells, fungi or tumor cells, due to expression, preferential expression or overexpression of a receptor for the ligand, accessible for binding, on the pathogenic cells. Acceptable binders include folic acid, analogs of folic acid and other folate receptor-binding molecules, other vitamins, peptide ligands identified from library screens, tumor-specific peptides, tumor-specific aptamers, tumor-specific carbohydrates, tumor-specific monoclonal or polyclonal antibodies, Fab orscFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, 6-opioid receptor ligands, cholecystokinin A receptor ligands, ligands specific for angiotensin AT1 or AT2 receptors, peroxisome proliferator-activated receptor y ligands, 13-lactam antibiotics, small organic molecules including antimicrobial drugs, and other molecules that bind specifically to a receptor preferentially expressed on the surface of tumor cells or on an infectious organism, or fragments of any of these molecules.

If the binder of the invention is a protein or peptides its length preferably varies between very few and more than hundred amino acid residues. Preferably, the length of the oligopeptide is between 1 and 75 amino acid residues, more preferably between 3 and 25 amino acid residues. The binder may have a binding affinity to one or more target molecules, target cells or target tissue as e.g. bacteria, fungi or tumor cells. The oligopeptides of the invention preferably is a synthetic peptide.

Examples of binders are given in Table 1.

Examples of sequences of preferred peptide binders are: CGLIIQKNEC; CNAGESSKNC; Dhb-pLDIK; Dhb-pLDI; WIFPWIQL; WDLAWMFRLPVG; VVISYSMPD; cyclo (RGDfK); RGDfK; RGDWXE; GGHGRVLWPDGWFS-LVGISP; YHWYGYTPQNVI; TACHQHVRMVRP; NLL-MAAS; DUP-1; HEWSYLAPYPWF; HTFEPGV; cyclo (SRESPHP); SRESPHP; KCCYSL; LTVXPWY; CSDSWHYWC; CSDxxHxWC; EDYELMDLLAYL; cyclo (CVGNDNSSC); CVGNDNSSC; TTPRDAY; VHLGYAT; CSNRDARRC; CXNXDXR(X)/(R)C; SWKLPPS; IAG-LATPGWSHWLAL; AWYPLPP; VPWMEPAYQRFL; EPAYQR; KSLSRHDHIHHH; TNSLP; YYGLAE-VDAGGS; MQLPLAT; MXXP.

Examples of target structures that can be targeted with these peptide binders are: fibrin-fibronectin complex; alpha-4-beta-1 integrin; alpha-v-beta-5 integrin; alpha-v-beta-3 integrin; alpha-3-beta-1 integrin; Glucose-regulated protein 78 (GRP78); EGFR; EGFRvIII; EphA2 receptor; Interleukin-6 Receptor (gp80, CD126); Tie2; Her-2 (human ErbB-2); Human vascular endothelia growth factor receptor 3 (VEGFR-3); FGF receptor; other cell-surface tumor markers.

Examples of tumors that can be specifically targeted with these peptide binders are: solid tumors; lymphomas; non-Hodgkin's lymphoma; colorectal cancers; prostate cancer; colon cancer; thyroid cancer; breast cancer; pankreatic cancer, ovarian cancer; follicular thyroid carcinoma; anaplastic thyroid carcinoma, mammary carcinoma, cervix carcinoma, prostate carcinoma; neoplastic vessels; hepatoma; hepatocellular carcinoma; bladder cancer; peritoneal tumors of gastric cancer; neuroblastoma; melanoma.

A further list of examples for target molecules of the present invention is provided in table 2.

As described above, the multifunctional compounds of the invention comprise a binder and an effector which are operably linked. The linkage ("linker") can be constituted by one covalent or functionally comparable bond as e.g. streptavidin/avidin or other complexing agents. The linker can also provide linkage between binder molecules themselves and also between effector molecules themselves as e.g. in the case of dendrimer linkers.

Different Possible Structures to Design a Multifunctional Compound are Inter Alia:

Structure of the active substance=Binder+effector+linker

Single binder+single effector+linear linker

Two or more same binders (avidity)+single effector+linear linker

Two or more different binders (avidity/selectivity/multivalency)+single effector element+linear linker One or more same or different binders+two or more same effectors (potency)+linear linker One or more same or different binders+two or more different effectors (potency/selectivity)+linear linker One or more same or different binders+one or more same or different effectors+branched linker (tentacle-like structure)

Examples for a linker of the present invention comprise direct coupling, small linker, statistical coupling by homooligofunctional linker, oligo-alcohols, -amines, -carboxylic acids, thiols, defined stochiometry by heterooligofunctional coupling element, polymer (hydrophilic and lipophilic polymer), statistical coupling by homomultifunctional linker, HPMA, polylysine, hydroxyethylcellulose, hydroxyethylstarch, aminodextran, copolymers, branched polymeric scaffolds, branched PEG, dendrimers, especially polylysine dendrimers, defined stochiometry by heterooligofunctional coupling, polypeptides, functionized activated polymers, PEG, polyurethanes.

The coupling of the units to the polymeric carrier unit, e.g. PEG, is performed using reactions known to the person skilled in the art. E.g. there are number of PEG and HES attachment methods available to those skilled in the art (see for example WO 2004/100997 giving further references, Roberts et al., 2002; U.S. Pat. No. 4,064,118; EP 1 398 322; EP 1 398 327; EP 1 398 328; WO 2004/024761). Dimerization of molecules via PEGylation, disulfide bridges or lysine side chains is described in WO 96/40772; WO 96/40749; WO 01/38342; WO 01/091780; WO 2004/101611; WO 2004/100997; WO 2004/101600; WO 2004/101606, Wrighton et al., 1997; Johnson et al., 1997). The mentioned methods combine monomeric peptides via a linker structure in order to obtain the desired dimeric or even multimeric molecules.

Embodiments

1. Single Binder+Single Effector; Linear Linker

In one embodiment of the invention, the multifunctional compound of the invention comprises a single binding element (binder) and a single effector which are linked via a linear linker. The binding element is an oligopeptide that has binding affinity to one or more target molecules, target cells or target tissue. Preferably the target molecule is a molecule expressed at the surface of cancer cells.

The length of the oligopeptide can vary between very few and more than hundred amino acid residues. Preferably, the length of the oligopeptide is between 1 and 75 amino acid residues, more preferably between 5 and 25 amino acid residues. The oligopeptide is typically comprised of at least some of the 20 natural amino acid residues. Alternatively, the oligopeptide is comprised of non-natural amino acid residues or a mixture of natural amino acid residues and non-natural amino acid residues and can also comprise non modified peptide bonds. Non-natural amino acid residues comprise non-canonical amino acids, for example b-Alanine, Carnitine, Citrulline, Homoarginine, Homocitrulline, Homocysteine, Homophenylalanine, Homoproline, Hydroxyproline, allo-Isoleucine, Isoserine, Ornithine, Phenylglycine, Phenylisoserine, allo-Threonine or a stereo-isomer (for example, D-instead of L-amino acids). In one embodiment, the oligopeptide is a linear molecule and is attached via the N- or the C-terminus to the linker. Alternatively, the peptide is cyclic or forms intramolecular disulfide bridges. In a further aspect, the oligopeptide comprises several copies of the same or different amino acid sequences attached to each other on the same oligopeptide molecule (peptide repeats).

In addition to peptidic backbone an artificial, non-natural backbone can be chosen for synthesis of peptidomimetics, conferring e.g. higher stability in-vivo or superior biophysical properties. examples of such backbones are phosphodiesters [Bioorg Med Chem. Lett. 1998 Mar. 3; 8(5):511-4. Solid-phase synthesis of peptidomimetic oligomers with a phosphodiester backbone. Lin P, Ganesan A.]

In a particular aspect of this embodiment, the oligopeptide has binding affinity to human EGFR (Epidermal Growth Factor Receptor) and/or variants, derivatives or homologues thereof. For example, the oligopeptide has binding affinity to the full-length EGFR or to the truncated receptor EGFRvIII (Epidermal Growth Factor Receptor variant III) or to both. EGFR is overexpressed in a number of pathogenic cell populations such as in colon cancer, head and neck cancer, ovarial cancer, pancreatic cancer, non-small cell lung cancer, breast cancer and glioblastoma.

Oligopeptides with binding affinity to EGFR are selected by screening among a library of peptide sequences for those that bind more selectively and with sufficient affinity to EGFR. Alternatively, peptide sequences can be used from natural ligands of the receptor, such as human EGF (Epidermal Growth Factor), or novel binders to EGFR such as anti-EGFR monoclonal antibodies.

In a further aspect of this embodiment, the oligopeptide has a length between 5 and 25 amino acid residues, and comprises one or more from the following group of sequences: GYTP; YGYTPQ; WYGYTPQN; HWYGYTPQNV; YHWYGYTPQNVI. In a preferred aspect, the oligopeptide has a length of 12 amino acid residues and comprises the sequence YHWYGYTPQNVI.

Abbreviations Amino Acid

| A | Ala | Alanine |
|---|-----|---------|
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |
| X | Xxx | any amino acid |

2. Linker Between the Binder and Effector

The linker of the present invention provides physical molecular linkage between the two domains, i.e. the binder and the effector.

Covalent Bond: Direct Linker

In one embodiment of the invention the binder and the effector are directly linked by a covalent bond. This can be established by incorporation of mutually reactive groups in both domains (i.e. the binder and effector respectively). Such mutually reactive and selective groups can be readily incorporated in the binder and effector. Examples of such mutually reactive groups are free cystein residues in both elements that form a stable disulfide bridge between the domains under oxidizing conditions. Another example of these mutually reactive would be a carbonyl-group in one domain and a amino-group in the other domain that form a hydrolytically unstable imine linkage by condensation that can be reduced by reaction the imine with cyanohdride compounds to yield a hydrolytically stable amine linkage between the compounds.

Small Linker

In another embodiment of the invention the binder or effector is connected by a low molecular weight linker. In a preferred embodiment this linker has a molecular weight of less than 1000 Dalton. In an even more preferred embodiment the low molecular weight linker has a molecular weight of less than 100 Dalton. Binder and effector may either simultaneously or sequentially reacted with the linker.

Statistical Coupling by Homooligofunctional Linker

In another embodiment of the invention the binder or effector is statistically coupled by a homooligofunctional linker as e.g. sebacic acid bis(N-succinimidyl)ester, 1,4-bis[3-(2-pyridyldithio)propionamido]butane, bis[2-(N-succinimidyl-oxycarbonyloxy)ethyl]sulfone, bis[2-(4-azidosalicylamido) ethyl]disulfide, dimethyl 3,3'-dithiopropionimidate dihydrochloride, or ethylene glycol disuccinate di(N-succinimidyl)ester.

Oligo-Alcohols, -Amines, -Carboxylic Acids, Thiols

In a preferred embodiment the low molecular weight linker as above carries only one type of reactive group that can be statistically coupled to the binder and effector yielding a mixture of the binder linked to the effector as described in the invention. It further yields in dimers of the binder as well as of the effector. These dimers can be separated by physicochemical methods know to a person skilled in the art.

Low molecular weight linker can be selected from the groups of oligo-alcohols, -amines, -carboxylic acids, thiols, carbonyls. In addition functionalized and activated homooligofunctional linkers can be selected having the advantage of higher reaction efficiencies and selectivities. In preferred embodiment these can be selected from the group of sebacic acid bis(N-succinimidyl)ester, 1,4-bis[3-(2-pyridyldithio) propionamido]butane, bis[2-(N-succinimidyl-oxycarbonyloxy)ethyl]sulfone, bis[2-(4-azidosalicylamido)ethyl]disulfide, dimethyl 3,3'-dithiopropionimidate dihydrochloride, ethylene glycol disuccinate di(N-succinimidyl)ester.

Defined Stochiometry by Heterooligofunctional Linker

In another preferred embodiment heterooligofunctional linkers are used to couple the binder and the effector. These heterooligofunctional linkers are characterized by having two or more different reactive chemical entities. These linkers avoid the formation of dimers of binder or effectors and therefore increase selectivity and yield of the coupling reaction.

In a preferred embodiment the heterooligofunctional linkers are selected from the group of saccharides, hydroxy carboxylic acids, amino acids. Heterooligofunctional linkers having more than two reactive groups can be used to prepare branched structures having more than on effector or more than one binder. Examples of such linkers are amino acids having side chains carrying carboxyl- or amino-groups like aspartic acid, glutamic acid or lysine.

Furthermore, functionalized and activated heterooligofunctional linkers are selected having the advantage of higher reaction efficiencies and selectivities. In preferred embodiment these are selected from the group of 3-(maleimido) propionic acid N-hydroxysuccinimide ester, 11-Maleimido) undecanoic acid N-succinimidyl ester.

The succinimide groups of these heterooligofunctional linkers are first reacted with an amine moiety of either the binder and/or effector under reaction conditions where the sulfhydryl specific maleimide moiety is essentially stable. The reaction yields a maleimide functionalized binder or effector that is in a second step reacted with the respective effector or binder functionalized with a free and unoxidized sulfhydryl group.

Polymeric Linker (Hydrophilic and Lipophilic Polymer)

In another preferred embodiment a polymeric linker is chosen, where the molecular weight of the linker is preferably between 1 kD and 100 kD, more preferably between 5 and 50 kD and most preferably between 10 and 30 kD. The linker polymer is any physiologically tolerated natural, modified natural or synthetic polymer.

In a preferred embodiment the lining polymer is selected from the group of polypeptides, polysaccharides, polyester, polyalcohols, polyether, polyurethane, polyacrylates or polynucleotides. In another preferred embodiment functionalized or activated derivates of the polymers are use as linkers of the invention.

Statistical Linking by Homomultifunctional Linker

Examples are HPMA (N-(2-hydroxypropyl)methacrylamide), polylysine, hydroxyethylcellulose, hydroxyethylstarch, aminodextran.

In an even more preferred embodiment the linker polymer is selected from the group of N-(2-hydroxypropyl)-methacrylamide copolymer, polylysine, hydroxyethylcellulose, aminodextran and poly-ethyleneoxide block copolymers. These polymers carry a multitude of reactive groups that can be reacted with the binder and effector in a statistical manner to yield a functionalized polymer characterized by physical linkage between the elements Copolymer Linker In another preferred embodiment a copolymer of the aforementioned polymers (regular, random, block or grafted) are used as a linker. The physical and physiological properties like viscosity, hydrophilicity, solubility of the polymer by providing physical combinations of such individual polymers. An example of such copolymer is the polymerization of ethylene oxide and propylene oxide ("Pluronic").

Branched Polymeric Scaffolds

In another preferred embodiment In another preferred embodiment a copolymer of the aforementioned polymers (regular, random, block or grafted) are used as a linker. are used as a linker.

Branched PEG

Linear as well as branched polymers and copolymers can be used in the invention. Branched polymers can be prepared as grafted copolymers or by direct polymerization initiated by a oligovalent starter. In a preferred embodiment branched polyethyleneglycols (multi-arm-PEGs) prepared by the latter method are used. These multi-arm-PEGs are commonly prepared with free hydroxyl moieties as chain terminators or subsequently modified to yield a functionalized, activated multi-arm-PEG.

Examples of such modifications are the incorporation of acrylate, amine, epoxide, isocyanate, succinimidyl glutarate, succinimidyl succinate. These can be reacted with reactive groups of the binder and effector to yield a molecular Dendrimers In an especially preferred embodiment dendrimers are used as linkers.

The dendrimers can preferably be polylysine based and coupled with different effectors and/or binders (substituents) and specifically be designed to allow for a defined ratio of two or more substituents forming parts of the dendrimers according to the selection of activators in synthesis. A protocol for preparation of mannosylated poly-L-lysine dendrimer peptide conjugates is described in Kantchev et al. Biopolymers (Pept Sci) 84:232-240, 2006. The Dendrimers can themselves be PEGylated with e.g. 50 kD PEGs, such PEGs carrying further effectors or binders. In a further preferred embodiment PEG derivatized binder and effector peptides are synthesized by solid phase and coupled to polymeric dendrimer scaffolds. If binder and effector peptide are coupled simultaneously to similar chemical moieties of the of polymeric dendrimer scaffold the reactions yields a reaction product with a statistical mixture of binder and effector elements coupled to the scaffold with the ration given by the choice of concentrations of educts a experimental conditions. If binder and effector peptide are coupled preferably consecutively to different chemical moieties of the of polymeric dendrimer scaffold the reactions yields a reaction product with a fixed stochiometry of binder and effector elements coupled to the scaffold with the ration given by the composition of the polymeric scaffold.

In another preferred embodiment the linker is polyethylene glycol (PEG).

In another preferred embodiment, linker combinations can be used to provide physical coupling between binder elements and effector elements. In one example heterooligofunctional linear linker molecules can be coupled to a homo-multifunctional polymeric scaffold to provide an intermediate hetero-multifunctional scaffold for coupling of binder and effector elements. In another embodiment homooligofunctional dendrimers with a multitude of coupled binder and effector elements can themselves be coupled by a heterooligofunctional linker to provide a substance with spatially segregated multivalent presentation of binder and effector elements providing higher binding avidity and signalling strength.

Other Examples are:

Defined stochiometry by heterooligofunctional coupling, polypeptides other functionized, activated polymers, polyurethanes.

3. Examples for Effectors

Effectors of the Innate Immune System

1. PAMPs (Pathogen Associated Molecular Patterns)—on viruses, fungi, and bacteria (1. LPS, 2. Agglutinates, 3. CpG-DNA, 4. N-formyl methionine peptides, 5. dsRNA, 6. Mannan and/or mannose residues (fucose), mannose containing polysaccharides, 7. Phosphocholine, 8. Glycolipid like molecule, 9. Flagellin, 10. Peptidoglycans).

An example of an effector mediating chemotactic response of human blood monocytes and human peritoneal macrophages is formyl-Met-Leu-Phe (fMLP) as described by Obrist et al. (Obrist et al. Int. J. Immunopharmacology, 5(4), 1983, 307-314).

1. The Leu-Asp-Leu-Leu-Phe-Leu (LDLLFL) peptide represents another class of FPR ligand. LDLLFL is a fragment of CKS-17; a protein derived from a conserved region of retroviral transmembrane proteins that has been shown to suppress several different components of immune response. LDLLFL is an antagonist of the FPR that competes for formyl-Met-Leu-Phe (fMLP) binding (Oostendorp et al., J. Immunol. 149: 1010-1015 (1992); Oostendorp et al., J Leukocyte Biol. 51: 282-288 (1992); Oostendorp et al., Eur. J. Immunol. 22: 1505-1511 (1995)).

2. The annexin I protein is another class of FPR ligand. The anti-inflammatory activity of annexin I has been observed in many systems, although the mechanism of these effects is not well understood. More recently, peptides derived from N-terminal proteolytic fragments of annexin I have been found to be FPR ligands. The 26 amino acid N-terminal peptide that is produced by the cleavage of full length annexin I by neutrophil elastase is an FPR agonist, although it acts at much higher concentrations than fMLP (Kd=740 [mu]m and 0.02 [mu]m, respectively). Tests of the effects of this agonist on cells expression FPR suggest that, although it is an agonist, this peptide may attenuate immune response by effectively inducing receptor desensitization.

Further Examples of Effectors

I. LPS from bacterial cell wall of Gram negative (rod shaped) bacteria a) Unmodified LPS b) t least one unmodified or modified monomer from LPS c) LPS mimetic molecule binding to Mindin/ECM and/or TLR4

II. Agglutinates from bacteria a) Unmodified Agglutinates b) Peptide with homology to at least a part of agglutinate sequence c) Peptide mimetic with homology to at least a part to agglutinate sequence d) Agglutinate mimetic binding to Mindin/ECM Peptide binding to Mindin/ECM Peptide mimetic binding to Mindin/ECM Any/Small molecule binding to Mindin/ECM III. CpG containing DNA-sequences a) Unmethylated or low frequency methylated bacterial DNA-sequence containing CpG repeats b) Unmethylated or low frequency methylated bacterial thiophoshphat-DNA-sequence containing CpG repeats c) DNA-sequence containing CpG repeats mimetic molecules binding TLR9

IV. N-formyl methionine a) Peptides starting with N-formyl methionine b) Peptide mimetic starting with N-formyl methionine c) Peptides containing at the C-terminus D-methionine d) Peptide mimetic containing at the C-terminus D-methionine e) Peptides inducing the FPR, FPRL1 or FPRL2 f) Peptide mimetic inducing the FPR, FPRL1 or FPRL2 g) Any/Small molecules inducing the FPR, FPRL1 or FPRL2 h) N-formyl methionine containing molecules

V. dsRNA of viruses a) unmodified dsRNA of viruses b) thiophospho-dsRNA of viruses c) dsRNA of viruses mimetic molecules binding TLR3

VI. Mannan/Mannose containing oligomers or polymers a) Unmodified Mannan and/or mannose residues (fucose) from yeast and bacterial cell walls b) At least one unmodified or modified monomer from mannan and/or mannose residues (fucose) from yeast and bacterial cell walls c) Mannan and/or mannose residues (fucose) from yeast and bacterial cell walls mimetic molecule binding to binding mannan binding lectin (MBL)

d) Unmodified mannose containing polysaccharides from bacteria and fungi e) At least one unmodified or modified monomer from mannose containing polysaccharides from bacteria and fungi f) Mannose containing polysaccharides from bacteria and fungi mimetic molecule binding to MMR (Macrophage mannose receptor)

VII. Phosphocholine from bacterial cell walls a) Unmodified, phosphocholine from bacterial cell walls b) Effector binds to CPR(C-Reactive Protein)

VIII. Glycolipid like molecule on pathogens a) Unmodified phosphocholine from bacterial cell walls b) binding TLR1 and/or TLR2/6 dimer IX. Flagellin from bacterial motor protein and virulence factor a) Unmodified flagellin b) Peptide with homology to at least a part of flagellin sequence c) Peptide mimetic with homology to at least a part to flagellin sequence d) Flagellin mimetic binding to Mindin/ECM Peptide binding to TLR5

Peptide mimetic binding to TLR5

Any/Small molecule binding to TLR5

X. Peptidoglycans from bacterial cell walls, especially gram+
a) Unmodified Peptidoglycans from bacterial cell walls, especially gram+
b) At least one unmodified or modified monomer from Peptidoglycans from bacterial cell walls, especially gram+
c) Peptidoglycans from bacterial cell walls, especially gram+, mimetic molecule binding to TLRs and NODs, especially to NOD proteins (NOD2 and NOD2)
XI. Major fimbrial subunit of thin curled fimbriae (CsgA) from *S. Typhimurium* Toll-like receptor (TLR) 2/CD14
XII. Helminth carbohydrate, lacto-N-fucopentaose III (LNF-PIII) functions as an innate Th2 promoter via its action on murine dendritic cells, with the alpha1-3-linked fucose required for this activity. Neoglycoconjugate lacto-N-fucopentaose III (12-25 molecules)-dextran (LNFPIII-Dex) activates dendritic cells (DCs) via TLR4×
XIII. Synthetic compounds *Escherichia coli*-type tryacyl lipopeptide (Pam3CSSNA), *E. coli*-type lipid A (LA-15-PP), diaminopimelic acid containing desmuramyl peptide (gamma-D-glutamyl-meso-DAP; iE-DAP), and muramyl-dipeptide (MDP) binding TLR2, TLR4, nucleotide-binding oligomerization domain (NOD)1 and NOD2
XIV. Yeast zymosan activates TLR2/TLR6 heterodimers, whereas *Saccharomyces cerevisiae*- and *C. albicans*-derived mannan seems to be detected by TLR4. Phospholipomannan, present in the cell surface of *C. albicans* has been shown to be recognized by TLR2, while TLR4 mainly interacts with glucuronoxylomannan, the major capsular polysaccharide of *C. neoformans*. MyD88 has been implicated in TLR signalling of linear (1->3)-beta-D-glucan, and of beta-glucan from *P. carinii*.

XV. Elongation factor Tu (EF-Tu), the most abundant bacterial protein, N-acetylated in *Escherichia coli*, N-acetylated peptide comprising the first 18 amino acids, termed elf18, is fully active as inducer of defense responses
XVI. Outer membrane protein A from *Klebsiella pneumoniae* (KpOmpA) binding TLR2
XVII. Fimbriae (from *Porphyromonas gingivalis*), which function as a surface adhesion; although TLR2 and TLR4 mediate cellular activation in response to fimbriae, other PRRs, namely CD14 and CD11b/CD18, are involved in the recognition of fimbriae.
XVIII. imidazoquinolines
XIX. mycoplasmal lipoprotein binding TLR6 and TLR2
XX. Acylated lipopeptides, e.g. diacylated mycoplasmal lipopeptides, termed macrophage-activating lipopeptide 2 kDa (MALP-2) or triacylated bacterial lipopeptide
XXI. Phenol-soluble modulin secreted from *Staphylococcus epidermidis*; *Staphylococcus epidermidis* releases a group of peptides termed phenol-soluble modulin (PSM) that stimulate macrophages. The structure of 3 peptides (PSM alpha, PSM beta, and PSM gamma) have been described. We report a fourth peptide (PSM delta), which is a 23mer with the structure fMSIVSTIIEVVKTIVDIVKKFKK.

Further examples comprise proteins from the Complement cascade.

4. Particularly Preferred Embodiments

Particularly preferred embodiments are presented in table 3

TABLE 3

| no | binder (b) | linker (l) | effector (e) | remarks |
|---|---|---|---|---|
| 1 | peptide | linear PEG | N-formyl methionine peptide | — |
| 2 | peptide | branched PEG | N-formyl methionine peptide | different mixtures enable various b:e combinations |
| 3 | microprotein | linear PEG | N-formylmethionine peptide | b:e, or multiple b or e |
| 4 | microprotein | branched PEG | N-formyl methionine peptide | different mixtures enable various b:e combinations |
| 5 | peptidomimetic | linear PEG | N-formyl methionine peptide | b:e 1:1, or multiple b or e |
| 6 | peptidomimetic | branched PEG | N-formyl methionine peptide | different mixtures enable various b:e combinations |
| 7 | phosphothio-RNA or DNA | linear PEG | N-formyl methionine peptide | b:e 1:1, or multiple b or e |
| 8 | phosphothio-RNA oder DNA | branched PEG | N-formyl methionine peptide | different mixtures enable various b:e combinations |
| 9 | b of no. 1-8 | l of no. 1-8 | peptidomimetic | e is bases on N-formyl methionine peptides |
| 10 | b of no. 1-8 | L of no. 1-8 | small molecules | imidazoquinolines or phosphocholine, etc |
| 11 | b of no. 1-8 | l of no. 1-8 | mannose, fucose, N-acetly glucosamine, N-acetyl galactosamine, polyguanylic acid (polyG) | terminale mannose, mannan or oligosaccharid with mannose residues etc. |

TABLE 3-continued

| no | binder (b) | linker (l) | effector (e) | remarks |
|---|---|---|---|---|
| 12 | b of no. 1-8 | hydrophile (linear) polymers | E of no. 1-12 | PEG or PEG derivatives, HPMA, polylysine, hydroyethylclellulose, hydroxyethylstärke, aminodextran, etc |
| 13 | B of no. no. 1-8 | hydrophile branched polymers | E of no. 1-12 | branched PEG or dendrimers |
| 14 | B of no. 1-8 | Polymers | E of no. 1-12 | polyalcohols, polyether, polyurethane, polyacrylates or polynucleotides |
| 15 | b of no. 1-8 | Homooligofunctional linker | E of no. 1-12 | |
| 16 | b of no. 1-8 | Heterooligofunctional linker | E of 1-12 | |
| 17 | b of no. 1-8 | l of no. 1-8 | peptide or peptidomimetic | FL2 induce FPRL2 Migeotte, I et al. JExpMed 2006 |
| 18 | b of no. 1-8 | l of no. 1-8 | peptide or peptidomimetic with C-terminal D-Meth | Bae Y-S et al. Mol Pharmacol 64: 841-847, 2003 |

EXAMPLES

I. Manufacture

Manufacture of Binders
Peptides

Methods to produce oligopeptides an proteins in vitro are known to the person skilled in the art. Original protocols to provide such oligopeptides have been published by Merrifield in 1963 [R. B. Merrifield, *J. Am. Chem. Soc.* 85, 2149 (1963); B. D. Larsen et al, *J. Am. Chem. Soc.* 115, 6247 (1993); D. D. Smith et al, *J. Peptide Protein Res.* 44, 183(1994); M. J. O'Donnell et al., *J. Am. Chem. Soc.* 118, 6070 (1996).
Synthetic Peptide (Unnatural Amino Acids, Etc), Cyclic Peptides, Peptide Mimetics Numerous improvements and extensions to the protocols have been found giving this methods a high degree of flexibility. The improvements include the incorporation of unnatural aminoacids [Ishida, H., & Inoue, Y. (1999) Peptides that contain unnatural amino acids: Toward artificial proteins. Reviews on Heteroatom Chemistry, 19, 79-142; O'Donnell, M. J., Lugar, C. W., Pottorf, R. S., Zhou, C., Scott, W. L., & Cwi, C. L. (1997) Solid-phase synthesis of unnatural amino acids using unactived alkyl halides. Tetrahedron Lett., 38, 7163-7166; Scott, W. L., Zhou, C., Fang, Z., & O'Donnell, M. J. (1997) The solid phase synthesis of alpha,alpha-disubstituted unnatural amino acids and peptides (di-UPS). Tetrahedron Lett., 38, 3695-3698.] and the production of cyclic peptides [Zhang, L. S., & Tam, J. P. (1997) Synthesis and application of unprotected cyclic peptides as building blocks for peptide dendrimers. J. Amer. Chem. Soc., 119, 2363-2370.; Koppitz, M., Huenges, M., Gratias, R., Kessler, H., Goodman, S. L., & Jonczyk, A. (1997) Synthesis of unnatural lipophilic N-(9H-fluoren-9-yl-methoxy)carbonyl-substituted alpha-amino acids and their incorporation into cyclic RGD-peptides: A structure activity study. Helv. Chim. Acta, 80, 1280-1300.; Gobbo, M., Biondi, L, Cavaggion, F., Filira, F., Piek, T., Mantel, P., & Rocchi, R. (1997) Synthesis and biological activities of head-to-tail cyclic bradykinin analogues of varying ring size. Int. J. Peptide Prot. Res., 50, 336-341; Eichler, J., & Houghten, R. A. (1997) Synthesis of cyclic disulfide peptides: Comparison of oxidation methods. Protein Peptide Lett., 4, 157-164; Blackburn, C., & Kates, S. A. (1997) Solid-phase synthesis of cyclic homodetic peptides. Methods Enzymol., 289, 175-198, Tam, J. P., & Lu, Y. A. (1998) A biomimetic strategy in the synthesis and fragmentation of cyclic protein. Protein Sci., 7, 1583-1592.

While the incorporation of unnatural amino acids into the peptide sequence gives additional flexibility to the function (e.g. the binding properties) of a peptide it also provides additional means of introducing reactive and selective chemical functions.

Larger proteins can be efficiently synthesized by native chemical ligation of two or more smaller peptides with C-terminal thioesters and N-terminal cysteines [PNAS|Dec. 19, 2000|vol. 97|no. 26|14074-14078; Chemical synthesis and spontaneous folding of a multidomain protein: Anticoagulant microprotein Silman M. Hackeng, José A. Fernández, Philip E. Dawson, Stephen B. H. Kent, John H. Griffin]

Besides the versatile methods of solid-phase synthesis, biological systems are known to the person skilled in the art to produce oligopeptides and low molecular weight proteins [Protein Expr Purif. 2006 Apr. 25; Extracellular production of human cystatin S and cystatin SA by *Bacillus subtilis*. Akiba S, Hayashi Y, Hakamada Y, Endo K, Ara K, Kawai S, Saitoh E. 120aa]
Peptide Repeats Peptide repeats may be produced and purified with the methods listed above.
Microprotein (Cystine Knots, etc)

Microproteins can be efficiently produced by means of solid phase synthesis [Olga Avrutina, Hans-Ulrich Schmoldt, Harald Kolmar, Ulf Diederichsen, Fmoc-Assisted Synthesis of a 29-Residue Cystine-Knot Trypsin Inhibitor Containing a Guaninyl Amino Acid at the P1-Position, European Journal of Organic Chemistry, 2004, 23, 4931-4935], in addition methods to produce microproteins such as cysteine-knot-proteins are known [Schmoldt H U, Wentzel A, Becker S, Kolmar H. A fusion protein system for the recombinant production of short disulfide bond rich cystine knot peptides using barnase as a purification handle. Protein Expr Purif. 2005 January; 39(1):82-9.]

Immunoglobulin (Immunoglobulin Fragment, scFvs, Domains, Etc)

Human or animal immunoglobin proteins can be produced in mammalian cell lines [*Curr Opin Biotechnol.* 1995 October; 6(5):553-60. *Production of monoclonal antibodies in COS and CHO cells.* Trill J J, Shatzman A R, Ganguly S.] as well as in prokaryotic organisms [*Curr Opin Biotechnol.* 2004 August; 15(4):364-73. *Prokaryotic expression of antibodies and affibodies.* Fernandez L A.]

Oligonucleotide (DNA Oligonucleotide (Aptamers), RNA Oligonucleotide (Aptamers), Oligonucleotide Analogs (PNA, DNA/RNA Chimera, Etc)

DNA oligonucleotides and modified derivatives (e.g. phosphotiate DNA/RNA) can be synthesised in-vitro by solid phase methods with arbitrary sequence and lengths up to 30 to 80 nucleotides with excellent yield and purity. Methods are known to the expert [Caruthers M H, Beaton G, Wu J V, Wiesler W. *Chemical synthesis of deoxyoligonucleotides and deoxyoligonucleotide analogs. Methods Enzymol.* 1992; 211: 3-20.; Caruthers M H, Beaton G, Cummins L, Graff D, Ma Y X, Marshall W S, Sasmoru H, Norris P, Yau E K. *Synthesis and biochemical studies of dithioate DNA.; Ciba Found Symp.* 1991; 158:158-66; discussion 166-8.; Caruthers M H, Beaucage S L, Becker C, Efcavitch J W, Fisher E F, Galluppi G, Goldman R, deHaseth P, Matteucci M, McBride L, et al. *Deoxyoligonucleotide synthesis via the phosphoramidite method. Gene Amplif Anal.* 1983; 3:1-26.]

In addition to the incorporation of the natural bases (C, T, A, G, U) artificial bases can be incorporated in the oligonucleotide that facilitate the coupling of the oligonucleotide 5' aminolinker of selectable length, 3' aminolinker of selectable length, or thiol groups.

Manufacture of Linkers

Direct Linker

The binder and the effector can be covalently linked. Suitable reaction conditions for covalently linking various functionalities are known to the person skilled in the art [Henson G T., Bioconjugate techniques, Academic Press 1996]. They usually require activation of an element (domain) prior to reacting it directly with the other element (domain). Examples of such reaction schemes are activation of a carboxy moiety of one partner by carbodiimides and contacting the reactive intermediate with a second element carrying a amino-group [Hoare D G, Koshland D E, J. Am. Chem. Soc. 88, 2057; Chu, B C F, Kramer F R, Orgel L E, Nuc. Ac. Res. 14, 5591-5603].

Small Linker

Statistical coupling by homooligofunctional linkers, oligoalcohols, -amines, -carboxylic acids, thiols.

Low molecular substrates like diol, triols, diamines, dicarboxylic acids can be used as reactive scaffolds for the coupling of binder and effector. Examples of such low molecular weight scaffolds are e.g. gylcerol, hexanediamine, succinic acid. Usually after activation of the reactive groups these can be reacted with the binder and effector to yield a statistical mixture of reaction products.

Experimental condition can be found in [Henson G T., Bioconjugate techniques, Academic Press 1996]. IN addition to this a number if activated bifunctional linking groups are available that facilitate coupling of the elements, examples of these are Dithiobis(succinimidylpropionate), Disuccinimidyl suberate, Disuccinimidyl tartrate [Henson G T., Bioconjugate techniques, Academic Press 1996].

Defined Stochiometry by Heterooligofunctional Linker

Heterooligofunctional linkers can be used as reactive scaffold for the formation of stoichiometrically defined combinations of binder and effector. Such scaffolds are characterised by two orthogonal functional groups that can be individually coupled to binders and effectors.

Examples of such bifunctional scaffolds or alpha-aminoacids [NH2, COOH], hydroxy-acids [OH, COOH]. Methods of coupling these functionalities selectively and individually are known to the expert [Henson G T., Bioconjugate techniques, Academic Press 1996]. In addition a number of activated heterobifunctional linkers are known. Examples of these are N-succinimidyl 3-(2-pyridyldithio)propionate and derivatives thereof, succinimidlyoxycarbonyl-alpha-methyl-alpha-(2-pyridyldithio) toluene, succinimidyl-4-(p-maleimidophenyl)butyrate to react amine groups of one element with sulfhydryl-groups of the other element [Henson G T., Bioconjugate techniques, Academic Press 1996].

Polymer Linker (Hydrophilic and Lipophilic Polymer)

Statistical Coupling by Homomultifunctional Linker

HPMA

Polylysine

Hydroxyethylcellulose, hydroxyethylstarch

Aminodextran

Copolymers

High molecular weight polymeric scaffold can be employed to couple binding and effector elements in a statistical way. By activation of the polymeric scaffold and reaction of the scaffold with binding and reaction. branched polymeric scaffolds branched PEG dendrimers Defined stochiometry by heterooligofunctional coupling Polypeptides Functionized, activated polymers

PEG, polyurethanes in a most preferred embodiment the linker is polyethyleneglycol.

Linkers combinations and Copolymers

Manufacture of Effectors

Peptides and Immunostimulating Element

Oligomers that Stimulate the Innate Immune System

Oligo- and Polypeptides

Peptides

Unmodified peptides fM-Peptides

The methods described above can be applied to producing peptides. Modifications to the peptide can be incorporated by the use of non-natural amino-acids as monomers in the synthesis of the peptide.

In an alternative approach the synthesised peptide is modified after syntheses. This is preferably done before deprotection and release of the synthesised product from the solid phase to facilitate isolation of the reacted product after modification. With this synthetic approach e.g. N-Methyl-formylated Peptides can be generated by first synthesising the peptide sequence with the incorporation of an N-terminal methionine residue. This residue can then be reacted with 2,4,5-trichlorophenyl formate to yield the formylated product [PNAS 0.99(14); Jul. 9, 2002, Scott Baskerville and David P. Bartel, A ribozyme that ligates RNA to protein]. The product can then be purified by standard-methods know to the person skilled in the art like reverse-phase HPLC.

Peptidoglycans from Bacterial Cell Walls

Lipopeptides e.g. acylated lipopeptides, e.g. diacylated mycoplasmal lipopeptides or triacylated bacterial lipopeptide and tryacyl lipopeptide (Pam3CSSNA), diaminopimelic acid containing desmuramyl peptide (gamma-D-glutamyl-meso-DAP; iE-DAP), and muramyldipeptide (MDP)

Proteins From Bacteria

Agglutinates/adhesines from bacteria, e.g. Fimbrial subunit (CsgA) from *S. typhimurium* or Fimbriae (from *Porphyromonas gingivalis*), which function as a surface adhesion Flagellin from Bacterial N-acetylated elongation factors from bacteria, e.g. Tu (EF-Tu) from *E. coli*

Outer membrane proteins from bacteria, e.g. *K. pneumoniae* (KpOmpA)

Bacterial proteins can be produced in high yields and purity by standard methods of biotechnological production and protein purification methods known to the person skilled in the art [Sambook, Molecular Cloning: A Laboratory Manual, Third Edition—Cold Spring Harbor Laboratory Press (January 2001)]. Modified proteins that confer immunostimulating effects like N-formylated bacterial or heterologous proteins can by produced as described in [Protein Expr Purif. 2003 December; 32(2):317-22. Expression of N-formylated proteins in *Escherichia coli*. Spector S, Flynn J M, Tidor B, Baker T A, Sauer R T].

Proteins from Antibodies

Fc-part of an antibody

Proteins from Antigens

Antigens from neutralizing antibodies

Antigens inducing the complement cascade

Antigens from autoimmune reactions

Numerous methods are known to produce such proteins by heterologous expression in pro and eukaryotic hosts.

Oligonucleotides

CpG containing DNA from bacteria

The method of solid phase synthesis as described above can be applied.

dsRNA of viruses

Oligo- or Polycarbohydrates

Mannose containing Oligo- or Polycarbohydrates

Mannan and/or mannose residues (fucose) from yeast and bacterial cell walls

Lacto-N-fucopentaose III (LNFPIII) from Helminth modified oligo- or polycarbohydrates LPS from bacteria Glycolipid like molecule on pathogens Small molecules that stimulate the innate immune system Imidazoquinolines Phosphocholine Manufacture of the List of Embodiments as Provided in Table 3.

The manufacture of the list of preferred embodiments is described below. Each item below refers to the corresponding item in table 3. The binder and effector moieties as listed below are given as example only and are not meant to limit the scope of the invention. Other examples of binders are given in Table 1. Other examples of effectors are given above ("3. Examples for Effectors"). The person skilled in the art knows how to exchange binder moieties and effector moieties for other binder and effector moieties. In particular a person skilled in the art knows how to adapt conditions of peptide solid phase synthesis to synthesize peptides of other sequence, and how to adapt chemical coupling protocols if various peptide sequences are to be coupled to a specific reagent or solid support.

Peptide Binder: Linear PEG: N-Formyl Methionine

By methods of solid phase syntheses a peptide binder of sequence YHWYGYTPQNVIK is synthesized carrying a single, unique lysine residue at the C-terminus. With the methods of solid phase synthesis an effector of N-formyl-methionine carrying peptide of sequence form-MMYALFC carrying a single unique Cys residue at the C-terminal end of the peptide is synthesized. A multifunctional activated Maleimide-PEG-N-succinimidylester (MAL-PEG-NHS) NEKTAR Product Catalog, Item. No 2E4M0H02) is provided as linker molecule.

By standard biochemical methods described in detail in [Hermanson G T., Bioconjugate techniques, Academic Press 1996, 228-245] the binder peptide can first be reacted with the NHS-moeity of the linker to yield a reaction product (YHWYGYTPQNVIK)-PEG-MAL. Under these conditions the MAL-moeity of the linker is essentially stable in the absence of sulfhydryl functions. Competing with coupling to the epsilon-amino group of the lysine residue, coupling to the amino-terminus of the peptide can occur. After completion of the reaction excess educt is removed by chromatographic methods [Hermanson G T., Bioconjugate techniques, Academic Press 1996, 228-245] and the purified reaction product YHWYGYTPQNVIK-PEG-MAL is subsequently reacted with the effector peptide form-MMYALFC to yield the desired reaction product YHWYGYTPQNVIK-PEG-(form-MMYALFC).

Peptide:branched PEG:N-FormylMethione.

By methods of solid phase syntheses a peptide binder of sequence YHWYGYTPQNVIK is synthesized carrying a single, unique Lysine residue at the C-terminus. With the methods of solid phase synthesis a effector peptide of N-formyl-methionine carrying peptide of sequence form-MMYALFK carrying a single unique Lys residue at the C-terminal end of the Peptide is synthesized. As a linker molecule a 4-Arm PEG-Succinimidyl Glutarate (Item. No P4SG-20, SunBio 57 Claremont Avenue, Orinda, Calif. 94563, USA) is provided as an activated linker. The peptide binder and the peptide effector are reacted simultaneously with the activated linker by standard biochemical methods described in detail in [Hermanson G T., Bioconjugate techniques, Academic Press 1996, 228-245]. The reaction yields a product of the general composition $(YHWYGYTPQNVIK)_x$-PEG-(form-MMYALFK)$_y$, where $x+y<=4$. The stoichiometric factors x and y can be determined by the experimenter by choosing the starting concentration of binder peptide and effector peptide appropriately. Competing with coupling to the epsilon-amino group of the lysine residue of the binder peptide, coupling to the amino-terminus of the peptide can occur.

Microprotein:linear PEG:N-FormylMethionine

By methods cited in [He-Shu Lu et al, Crystal Structure of Human Epidermal Growth Factor and Its Dimerization, THE JOURNAL OF BIOLOGICAL CHEMISTRY, Vol. 276, No. 37, Issue of September 14, pp. 34913-34917, 2001] a EGF microprotein binder is synthesized carrying a Lysine residue at the C-terminus. By methods of solid phase syntheses a microprotein binder of the general sequence form-MMYALFC is synthesized carrying a Cys residue. A multifunctional activated Maleimide-PEG-N-succinimidylester (MAL-PEG-NHS) NEKTAR Product Catalog, Item. No 2E4M0H02) is provided as linker molecule. By standard biochemical methods described in detail in [Hermanson G T., Bioconjugate techniques, Academic Press 1996, 228-245] the binder peptide can first be reacted with the NHS-moeity of the linker to yield a reaction product EGF-PEG-MAL. Under these conditions the MAL-moeity of the linker is essentially stable in the absence of sulfhydryl functions. Competing with coupling to the epsilon-amino group of the lysine residue, coupling to the amino-terminus of the peptide can occur. After completion of the reaction excess educt is removed by chromatographic methods [Hermanson G T., Bioconjugate techniques, Academic Press 1996, 228-245] and the purified reaction product EGF-PEG-MAL is subsequently reacted with the effector peptide form-MMYALFC to yield the desired reaction product EGF-PEG-(form-MMYALFC).

Microprotein:branched PEG:N-FormylMethione.

By methods cited in [He-Shu Lu et al, Crystal Structure of Human Epidermal Growth Factor and Its Dimerization, THE JOURNAL OF BIOLOGICAL CHEMISTRY, Vol. 276, No. 37, Issue of September 14, pp. 34913-34917, 2001] a EGF microprotein binder is synthesized carrying a Lysine residue at the C-terminus. By methods of solid phase syntheses a microprotein binder of the general sequence form-MMY-ALFK is synthesized carrying a lysine residue. As a linker molecule a 4-Arm PEG-Succinimidyl Glutarate (Item. No P4SG-20, SunBio 57 Claremont Avenue, Orinda, Calif. 94563, USA) is provided as an activated linker. The peptide binder and the peptide effector are reacted simultaneously with the activated linker by standard biochemical methods described in detail in [Hermanson G T., Bioconjugate techniques, Academic Press 1996, 228-245]. The reaction yields a product of the general composition $(EGF)_x$-PEG-(form-$MMYALFK)_y$, where x+y<=4. The stoichiometric factors x and y can be determined by the experimentator by choosing the starting concentration of binder peptide and effector peptide appropriately. Competing with coupling to the epsilon-amino group of the lysine residue, coupling to the amino-terminus of the peptide can occur.

Peptidomimetic Binder:linear PEG:-FormylMethionine

By methods given in [Nat Chem. Biol. 2006 July; 2(7):381-9. Epub 2006 Jun. 11, Combinatorial chemistry identifies high-affinity peptidomimetics against alpha(4)beta(1) integrin for in vivo tumor imaging. Peng L, Liu R, Marik J, Wang X, Takada Y, Lam K S.] a peptidomimetic high affinity binder against alpha(4)beta(1) integrin is synthesized carrying an amino-linker. With the methods of solid phase synthesis an effector peptide of N-formyl-methionine carrying peptide of sequence form-MMYALFC carrying a single unique Cys residue at the C-terminal end of the Peptide is synthesized. A multifunctional activated Maleimide-PEG-N-succinimidy-lester (MAL-PEG-NHS) NEKTAR Product Catalog, Item. No 2E4M0H02) is provided as linker molecule. By standard biochemical methods described in detail in [Hermanson G T., Bioconjugate techniques, Academic Press 1996, 228-245] the binder peptide can first be reacted with the NHS-moeity of the linker to yield a reaction product binder-PEG-MAL. Under these conditions the MAL-moeity of the linker is essentially stable in the absence of sulfhydryl functions. Competing with coupling to the epsilon-amino group of the lysine residue, coupling to the amino-terminus of the peptide can occur. After completion of the reaction excess educt is removed by chromatographic methods [Hermanson G T., Bioconjugate techniques, Academic Press 1996, 228-245] and the purified reaction product binder-PEG-MAL is subsequently reacted with the effector peptide form-MMYALFC to yield the desired reaction product binder-PEG-(form-MMYALFC).

Peptidomimetic:branched PEG:N-FormylMethione.

By methods given in [Nat Chem. Biol. 2006 July; 2(7):381-9. Epub 2006 Jun. 11, Combinatorial chemistry identifies high-affinity peptidomimetics against alpha(4)beta(1) integrin for in vivo tumor imaging. Peng L, Liu R, Marik J, Wang X, Takada Y, Lam K S.] a peptidomimetic high affinity binder against alpha(4)beta(1) integrin is synthesized carrying an amino-linker. With the methods of solid phase synthesis a effector peptide of N-formyl-methionine carrying peptide of sequence form-MMYALFK carrying a single unique Lys residue at the C-terminal end of the Peptide is synthesized. As a linker molecule a 4-Arm PEG-Succinimidyl Glutarate (Item. No P4SG-20, SunBio 57 Claremont Avenue, Orinda, Calif. 94563, USA) is provided as an activated linker. The peptide binder and the peptide effector are reacted simultaneously with the activated linker by standard biochemical methods described in detail in [Hermanson G T., Bioconjugate techniques, Academic Press 1996, 228-245]. The reaction yields a product of the general composition $(binder)_x$-PEG-(form-$MMYALFK)_y$, where x+y<=4. The stoichiometric factors x and y can be determined by the experimentator by choosing the starting concentration of binder peptide and effector peptide appropriately. Competing with coupling to the epsilon-amino group of the lysine residue, coupling to the amino-terminus of the peptide can occur.

DNA Binder:linear PEG:N-FormylMethionine

By methods of solid phase syntheses a DNA aptamer of the general sequence $N_x$-spacer-SH is synthesized carrying a single, unique sulfhydryl residue at the 3' end. With the methods of solid phase synthesis a N-formyl-methionine peptide of sequence form-MMYALFK carrying a single unique Lys residue at the C-terminal end of the Peptide is synthesized. A multifunctional activated Maleimide-PEG-N-succinimidy-lester (MAL-PEG-NHS) NEKTAR Product Catalog, Item. No 2E4M0H02) is provided as linker molecule. By standard biochemical methods described in detail in [Hermanson G T., Bioconjugate techniques, Academic Press 1996, 228-245] the C-terminal Lysine of the effector peptide can first be reacted with the NHS-moeity of the linker to yield a reaction product form-MMYALFK-PEG-MAL. Under these conditions the MAL-moeity of the linker is essentially stable in the absence of sulfhydryl functions. After completion of the reaction excess educt is removed by chromatographic methods know to the person skilled in the art and the purified reaction product form-MMYALFK-PEG-MAL is subsequently reacted with the DNA aptamer NNNNN-spacer-SH to yield the desired reaction product form-MMYALFK-PEG-spacer-NNNNN.

DNA:branched PEG:N-FormylMethione.

By methods of solid phase syntheses a DNA aptamer of the general sequence $N_x$-spacer-SH is synthesized carrying a single, unique sulfhydryl residue at the 3' end. With the methods of solid phase synthesis a effector peptide of N-formyl-methionine carrying peptide of sequence form-MMYALFK carrying a single unique Lys residue at the C-terminal end of the Peptide is synthesized. As a linker molecule a 4-Arm PEG-Succinimidyl Glutarate (Item. No P4SG-20, SunBio 57 Claremont Avenue, Orinda, Calif. 94563, USA) is provided as an activated linker. The peptide binder and the peptide effector are reacted simultaneously with the activated linker by standard biochemical methods described in detail in [Hermanson G T., Bioconjugate techniques, Academic Press 1996, 228-245]. The reaction yields a product of the general composition (form-$MMYALFK)_y$-PEG-(spacer-$N_x)_z$ where z+y<=4. The stoichiometric factors x and y can be determined by the experimentator by choosing the starting concentration of binder peptide and effector peptide appropriately.

Peptide:linear PEG:N-Formylmethionie Peptidomimetic

By methods of solid phase syntheses a peptide binder of sequence YHWYGYTPQNVIK is synthesized carrying a single, unique Lysine residue at the C-terminus. With the methods of solid phase synthesis a N-formyl-methionine carrying peptidomimetic of sequence form-M-$X_n$C carrying a single unique Cys residue at the C-terminal end of the peptidomimetic effector is synthesized. A multifunctional activated Maleimide-PEG-N-succinimidylester (MAL-PEG-NHS) NEKTAR Product Catalog, Item. No 2E4M0H02) is provided as linker molecule. By standard biochemical methods described in detail in [Hermanson G T., Bioconjugate techniques, Academic Press 1996, 228-245] the binder peptide can first be reacted with the NHS-moeity of the linker to yield a reaction product (YHWYGYTPQNVIK)-PEG-MAL. Under these conditions the MAL-moeity of the linker is essentially stable in the absence of sulfhydryl functions. Competing with coupling to the epsilon-amino group of the lysine residue, coupling to the amino-terminus of the peptide can occur. After completion of the reaction excess educt is removed by chromatographic methods [Hermanson G T., Bioconjugate techniques, Academic Press 1996, 228-245] and the purified reaction product (YHWYGYTPQNVIK-)PEG-MAL is subsequently reacted with the peptidomimetic effector form-M-$X_n$C to yield the desired reaction product (YHWYGYTPQNVIK)-PEG-(form-M-$X_n$C).

Peptide:linear PEG:small molecule With the methods described above and known to the person skilled in the art a small molecule can be coupled to a linear PEG Multivalent Effector Dendrimer As described in detail in Kantchev et al. (Biopolymers. 2006; 84(2):232-40) pure, monodisperse third-generation mannosylated poly-L-lysine dendrimer-peptide conjugates using direct, machine-assisted Fmoc/t-Bu solid phase peptide synthesis can be prepared in order to provide for a multivalent effector dendrimer.

Binder and Effector Statistically Coupled to highMW Polymeric Scaffold

With the experimental procedures given in [Ulbrich K. et al.; Polymeric drugs based on conjugates of synthetic an natural macromolecules, J. of Controlled Release, 64, 2000, 63-79] a polymer precursor is prepared by copolymerisation of N-(2-hydroxypropyl)methacrylamide) and a methacryloyl-peptide-4-nitrophenylester of the general composition MA-(Xn)-oNP. By methods of solid phase syntheses a peptide binder of sequence YHWYGYTPQNVIK is synthesized carrying a single, unique Lysine residue at the C-terminus. With the methods of solid phase synthesis an effector peptide of N-formyl-methionine carrying peptide of sequence form-MMYALFK carrying a single unique Lys residue at the C-terminal end of the Peptide is synthesized. By the methods given in [Ulbrich K. et al.; Polymeric drugs based on conjugates of synthetic an natural macromolecules, J. of Controlled Release, 64, 2000, 63-79] the polymeric precursor is then sequentially reacted with binder peptide and effector peptide that aminolytically reacts with the oNP moieties of the polymer. The product of the reaction is a stable high-MW polymeric drug with a statistical distribution of binder and effector functions, where the mean binder and effector substitution grades of the polymer are given by the experimental choice of the concentrations reactants in preparation of the polymer precursor an aminolytic coupling of binder and effector groups.

Copolymerisation (meth-acrylate) of Elements a) With the experimental procedures given in [Ulbrich K. et al.; Polymeric drugs based on conjugates of synthetic an natural macromolecules, J. of Controlled Release, 64, 2000, 63-79] a polymer precursor is prepared by copolymerisation of N-(2-hydroxypropyl)methacrylamide) and a methacryloyl-binder peptide-4-nitrophenylester of the general composition MA-(YHWYGYTPQNVI) and a methacryloyl-effector peptide-4-nitrophenylester of the general composition form-MMYALF-MA. The product of the reaction is a stable high-MW polymeric drug with a statistical distribution of binder and effector functions, where the mean binder and effector substitution grades of the polymer are given by the experimental choice of the concentrations of reactants in preparation of the polymeric substance.

b) With the experimental procedures given in [Jackson D C, Free radical polymerisation of synthetic peptides into polymeric immunogens, Vaccine, 15(15), 1697-1705, 1997] a peptide binder of sequence Acryloyl-YHWYGYTPQNVI is synthesized carrying a Acryloyl-residue at the N-terminus. With the experimental procedures given in [Jackson D C, Free radical polymerisation of synthetic peptides into polymeric immunogens, Vaccine, 15(15), 1697-1705, 1997] a peptide effector of sequence Acryloyl-YHWYGYTPQNVI is synthesized carrying a Acryloyl-residue at the N-terminus. With the experimental procedures given in [Jackson D C, Free radical polymerisation of synthetic peptides into polymeric immunogens, Vaccine, 15(15), 1697-1705, 1997] the peptide effector and the effector peptide are copolymerised to yield the active polymeric substance.

Peptide Binder:polylysine:mannosyl residues a) With the methods given in [Kantchev E A B et al., Direct Fmoc/tert-Bu solid phase synthesis of Octomannosyl Poylylsine dendrimer-peptide conjugates, Biopolymers. 2006; 84(2):232-40] an active substance of the general composition YHWYGYTPQNVI-(Polylysine-dendrimer)-(Mannosyl)$_8$ is synthesized with the moiety YHWYGYTPQNVI being a binder peptide, polylysine being the linker element and mannosyl-residues being the effector element.

b) With the methods given in [Kantchev E A B et al., Direct Fmoc/tert-Bu solid phase synthesis of Octomannosyl Poylylsine dendrimer-peptide conjugates, Biopolymers. 2006; 84(2):232-40] a active substance of the general composition YHWYGYTPQNVI-(Polylysine-dendrimer)-(form-MMYALF)$_8$ is synthesized with the moiety YHWYGYTPQNVI being a binder peptide, polylysine being the linker element and form-MMYALF being the effector peptide.

c) With the methods given in [Kantchev E A B et al., Direct Fmoc/tert-Bu solid phase synthesis of Octomannosyl Poylylsine dendrimer-peptide conjugates, Biopolymers. 2006; 84(2):232-40] a active substance of the general composition YHWYGYTPQNVI-(Polylysine-dendrimer)-(form-MMYALF)$_8$ is synthesized with the moiety YHWYGYTPQNVI being a binder peptide, polylysine being the linker element and form-MMYALF being the effector element.

d) With the methods given in [Kantchev E A B et al., Direct Fmoc/tert-Bu solid phase synthesis of Octomannosyl Poylylsine dendrimer-peptide conjugates, Biopolymers. 2006; 84(2):232-40] a active substance of the general composition WKYMVm-(Polylysine-dendrimer)-(YHWYGYTPQNVI)$_8$ is synthesized with the moiety YHWYGYTPQNVI being a binder peptide, polylysine being the linker element and WKYMVm being the effector element.

Peptide Binder:linear PEG:N-FormylMethionine

By methods of solid phase syntheses a peptide binder of sequence YHWYGYTPQNVIK is synthesized carrying a single, unique Lysine residue at the C-terminus. With the methods of solid phase synthesis an effector peptide of N-formyl-methionine carrying peptide of sequence form-MMYALFK carrying a single unique Lys residue at the C-terminal end of the Peptide is synthesized. A bifunctional activated N-succinimidylester-PEG-N-succinimidylester (NHS-PEG-NHS) NEKTAR Product Catalog, Item. No 4K4K0L02) is provided as linker molecule. By standard biochemical methods described in detail in [Hermanson G T., Bioconjugate techniques, Academic Press 1996] the binder peptide and the effector peptide are simultaneously reacted with the linker molecule provided. After completion of the reaction the resulting mixture of molecular product species (YHWYGYTPQNVIK-PEG-(form-MMYALFK), YHWYGYTPQNVIK-PEG-(YHWYGYTPQNVIK), form-MMYALFK-PEG-(form-MMYALFK), YHWYGYTPQNVIK-PEG, form-MMYALFK-PEG) and excess educt are separated by standard chromatographic methods known to the person skilled in the art to isolate the desired product YHWYGYTPQNVIK-PEG-(form-MMYALFK).

Peptide:linear PEG:Peptidomimetic FPRL2 binder

By methods of solid phase syntheses a peptide binder of sequence YHWYGYTPQNVIK is synthesized carrying a single, unique Lysine residue at the C-terminus. With the methods of solid phase synthesis a Peptidomimetic FPRL2 binder of sequence $(X_n)C$ [see for reference: Migeotte I. et al., Identification and characterization of an endogenous chemotactic ligand specific for FPRL2 The Journal of Experimental Medicine Vol. 201, No. 1, Jan. 3, 2005 83-93] carrying a single unique Cys residue at the C-terminal end of the peptidomimetic effector is synthesized. A multifunctional activated Maleimide-PEG-N-succinimidylester (MAL-PEG-NHS) NEKTAR Product Catalog, Item. No 2E4M0H02) is provided as linker molecule. By standard biochemical methods described in detail in [Hermanson G T., Bioconjugate techniques, Academic Press 1996, 228-245] the binder peptide can first be reacted with the NHS-moiety of the linker to yield a reaction product (YHWYGYTPQNVIK)-PEG-MAL. Under these conditions the MAL-moeity of the linker is essentially stable in the absence of sulfhydryl functions. Competing with coupling to the epsilon-amino group of the lysine residue, coupling to the amino-terminus of the peptide can occur. After completion of the reaction excess educt is removed by chromatographic methods [Hermanson G T., Bioconjugate techniques, Academic Press 1996, 228-245] and the purified reaction product (YHWYGYTPQNVIK-)PEG-MAL is subsequently reacted with the peptidomimetic FPRL2 binder to yield the desired reaction product (YHWYGYTPQNVIK)-PEG-($(X_n)$C).

Peptide:linear PEG:Peptid with c-Terminal D-Meth

By methods of solid phase syntheses a peptide binder of sequence YHWYGYTPQNVIK is synthesized carrying a single, unique Lysine residue at the C-terminus. With the methods of solid phase synthesis a effector peptide of sequence CWKYMVm [see for reference: Yang D, Chen Q, Gertz B, He R, Phulsuksombati M, Ye R D, Oppenheim J J., Human dendritic cells express functional formyl peptide receptor-like-2 (FPRL2) throughout maturation, J Leukoc Biol. 2002 September; 72(3):598-607] carrying a D-Methione (m) residue at the C-terminal and carrying a single unique Cys residue at the N-terminal end of the peptidomimetic effector is synthesized. A multifunctional activated Maleimide-PEG-N-succinimidylester (MAL-PEG-NHS) NEKTAR Product Catalog, Item. No 2E4M0H02) is provided as linker molecule. By standard biochemical methods described in detail in [Hermanson G T., Bioconjugate techniques, Academic Press 1996, 228-245] the binder peptide can first be reacted with the NHS-moeity of the linker to yield a reaction product (YHWYGYTPQNVIK)-PEG-MAL. Under these conditions the MAL-moeity of the linker is essentially stable in the absence of sulfhydryl functions. Competing with coupling to the epsilon-amino group of the lysine residue, coupling to the amino-terminus of the peptide can occur. After completion of the reaction excess educt is removed by chromatographic methods [Hermanson G T., Bioconjugate techniques, Academic Press 1996, 228-245] and the purified reaction product (YHWYGYTPQNVIK-)PEG-MAL is subsequently reacted with the effector peptide of sequence CWKYMVm to yield the desired reaction product (YHWYGYTPQNVIK)-PEG-(CWKYMVm).

Dendrimer by Solid Phase Synthesis

With methods of solid phase a binder peptide is synthesized with sequence YHWYGYTPQNVIK-PEG-COON where a Polyethylenglycolspacer (Novabiochem, Cat. No. 01-63-0150 Fmoc-NH-(PEG)27-COOH) is connected to C-terminus of the binder peptide. The peptide is cleaved from the solid phase support without deprotection. With methods of solid phase a N-formyl-methionine-effector peptide is synthesized with sequence form-MMYALF-PEG-COOH where a Polyethylenglycolspacer (Novabiochem, Cat. No. 01-63-0150 Fmoc-NH-(PEG)27-COOH) is connected to C-terminus of the effector peptide. The peptide is cleaved from the solid phase support without deprotection.

With the methods given in [Kantchev E A B et al., Direct Fmoc/tert-Bu solid phase synthesis of Octomannosyl Polylysine dendrimer-peptide conjugates, Biopolymers. 2006; 84(2):232-40] a polylysine dendrimer is synthesised. The protected binder peptide (YHWYGYTPQNVIK-PEG-COOH) and the protected effector peptide (form-MMYALF-PEG-COOH) are simultaneously reacted with the Polylysine dendrimer to yield the desired reaction product (form-MMYALF-PEG)x-COOHPolylysine-(YHWYGYTPQNVIK-PEG-COOH)y with the general stoichiometric coefficients x and y by the choice of experimental conditions and concentrations of the binder and effector peptide provided.

Linear Peptide Conjugates

In an alternative approach peptide conjugates can be synthesized by methods known to the person skilled in the art. The compound comprises one or more binder peptides, a linker peptide and one or more effector peptides, all linked by peptide bonds. In a preferred embodiment, the effector peptide is form-MMYALF, the linker peptide is polylysine K(n), and the binder peptide is YHWYGYTPQNVI. Preferably, a linear peptide conjugate is synthesized having the sequence form-MMYALF-(K)n-YHWYGYTPQNVI, with n in the range of 0-50, preferably in the range of 0-10. In the case of n=0 the binder and the effector moieties are linked by a single peptide bond. In another preferred embodiment, the effector peptide is formyl-Met-Leu-Phe (fMLP), the linker peptide is polylysine K(n), and the binder peptide is AWYPLPP, with n in the range of 0-50, preferably in the range of 0-10.

Branched Peptide Conjugates

In an alternative approach peptide conjugates can be synthesized by methods known to the person skilled in the art comprising one or more binder peptides, a linker peptide and one or more effector peptides linked by peptide and amide bonds. Choosing effector peptide form-MMYALF, the linker peptide polylysine K(n), the binder peptide YHWYGYTPQNVI, a linear peptide conjugate is synthesized, having the sequence form-MMYALF-(K)n-YHWYGYTPQNVI with n in the range of 1-50 preferably in the range of 1-10. As a second substrate the binder peptide YHWYGYTPQNVI is synthesized by methods known to the person skilled in the art. The binder peptide is subsequently reacted with the linear peptide conjugate by CDI coupling as described in detail in Hermanson et al, 1996 (Hermanson G T., Bioconjugate techniques, Academic Press 1996) yielding an amide linkage between the epsilon amino function of the lysine residues of the linker region to the carboxy terminus of the binder peptide resulting in a branched peptide conjugate of the general composition form-MMYALF-(K)n-(YHWYGYTPQNVI)m-YHWYGYTPQNVI wherein n is in the range between 1 and 50, preferably in the range between 1 and 10, and m is in the range between 1 and n. The number of branches m is determined by the experimentator by choosing reaction conditions, especially by varying the concentration of the substrates.

Branched Peptides by Solid Phase Synthesis with Chemical Coupling

A multiple peptide dendrimer is synthesised by solid phase synthesis carrying 8 binding peptides of sequence NH2-MQLPLAT-COOH coupled to a three level lysine core according to Tam et al, 1988 (Tam, J. P., PNAS USA 85, 5409-5413, 1988). With methods of solid phase synthesis an effector peptide is synthesized with the sequence form-MLP-COOH. The effector peptides are subsequently reacted with the branched peptide dendrimer by CDI coupling as described in detail in Hermanson et al, 1996 (Hermanson G T., Bioconjugate techniques, Academic Press 1996) yielding an amide linkage between the alpha amino group of the binder peptide dendrimer to the carboxy terminus of the effector peptide resulting in a branched peptide conjugate of general composition (fMLP)m-(MQLPLATGGG)8-(K)4-(K)2-K-betaA. The number of branches m is determined by the experimentator by choosing reaction conditions, resulting in substoichiometric coupling of the effector peptide to the binder peptide dendrimer.

Branched Peptides by Solid Phase Synthesis

Branched peptides are directly prepared by solid phase syntheses with the methods described by Sheridan et al. (Sheridan J M, Hayes G M, Austen B M., Pept Sci. 1999 December; 5(12):555-62). By using Dde protected Lysine residues as branching points in the synthesis of peptides a branched conjugate of formula fMLPK-(NH2-MQLPLAT)-GGGK-(NH2-MQLPLAT)-I-COOH is synthesized containing the effector fMLP-COOH and two binders NH2-MQL-PLAT-COOH.

Reagents: TI(tfa)3 (Sigma:Aldrich, UK), Fmoc-amino acids (PE Applied Biosystems, UK and Alexis Corporation, UK), PyBOP (Calbiochem-Novabiochem (UK) Ltd, UK), hydrazine monohydrate (Sigma:Aldrich), 1% TNBS:DMF and acetic anhydride (Fluke Chemicals, UK). All solvents (and DIEA) are purchased from Sigma:Aldrich.

Solid phase Fmoc: tBu methodology is used on pre-swelled Fmoc-PAL-PEG-PS resin (0.19 mmol:g) (PE Applied Biosystems) in DMF under continuous flow, on a Milligen 9050 machine programmed to perform Fmoc-amino acid:PyBOP:DIEA couplings for 45 min, and Fmoc deprotection reactions (in 20% piperidine in DMF, v:v) for 9 mins. Fmoc deprotection was monitored at 365 nm. Where required, couplings or acetylations were judged complete with TNBS. Selective deprotection of Lys(Dde) is done under continuous flow, using 2% hydrazine:DMF (v:v) at 3 ml:min through a 1 cm diameter reaction column. Dde removal is monitored at 365 nm, confirmed with TNBS, and the peptide resin then washed with DMF. Final cleavage from the resin and removal of TFA-labile protecting groups use a cocktail of 95% TFA:2.5% TIS:2.5% H2O (v:v) for 2 h at r.t. Cleaved resin is removed by filtration, washed twice with 4 ml of neat TFA and the combined filtrates evaporated to 2 ml. Ice cold diethyl ether (40 ml) is added to cause peptide precipitation and the mixture centrifuged at 1000 rpm for 5 min. The ethereal solution is decanted and four further diethyl ether extractions are performed. Analytical HPLC is performed on a Nucleosil 5 C8 300 (150_4.6 mm) column with gradients of solvents, A 0.1% aq. TFA and B 0.1% TFA:acetonitrile (v:v), run at 1 ml:min with 215 nm UV detection. Preparative HPLC use the same solvents on a Vydac C4 column (Hichrom Ltd, UK), run with 225 nm UV detection. The extents of reaction completions are estimated from the HPLC area.

Preparation of Linear Peptide form-M-L-P-K(Ddee)-G-G-G-K(Dde)-I-PALPEG-PS: To the resin Fmoc-amino acids: Py-BOP:DIEA are sequentially coupled in the proportions 4:4:8 w.r.t. mmol peptide-resin. The first Ile is double-coupled to the resin. This protected peptide-resin is used as starting material for the two synthetic routes to the hinge-loop peptide.

Addition of binder peptide to linear effector loop peptide: formyl-M-L-P-K(Ddee)-G-G-G-K(Dde)-I-PALPEG-PS is prepared as described and is swollen in DMF and selective deprotection of Lys-(Dde) is performed under continuous flow as described above. Amino acids are then sequentially coupled (Fmoc-amino acids:PyBOP:DIEA, 8:8:16 w.r.t. mmol peptide-resin) under continuous flow. The resin is washed 3 with DMF, DCM, and MeOH and dried under high vacuum for 5 h. Final cleavage and isolation of the crude peptide is achieved using the TFA cocktail and diethyl ether trituration as above.

II. Assays

1. Assessment of Activation of Mannose Receptor

To measure the activation potential of mannose, mannan, mannose containing molecules, fucoidan, polyguanylic acid (polyG) chemically modified and unmodified low density lipoproteins (LDL) or any other potential effector molecule, several assays can be employed. Some of them focus on the possible binding of MBL (Mannose binding lectin), MR (Mannose receptor) or the scavenger receptors (SR)SR-A and SR-B.

Some of them use whole immune cells without knowing which mechanism is important for the activation of such cells. For example, production of intracellular cytokines by monocytes and MDM (monocyte-derived macrophages) stimulated by PAMPs is a suitable method [Mytar B; Inflamm Res. 2004 March; 53(3):100-6. Epub 2004 Feb. 16].

Binding and internalization assays can be carried out by using mannose labelled molecules [Lew D B; Clin Invest. 1994 November; 94(5):1855-63].

2. Activation of FPR Receptors

In the international laid open WO0031261 A1 a method is described, which is suitable for screening polypeptides or non-peptidic compounds which possibly induce receptor signaling of FPRL-1. The assay described therein can score for test compounds which potentiate the induction response generated by interaction of the FPRL-1 receptor and agonists.

The method disclosed in WO0031261 can be applied for identifying effectors with the potential to modify FPR, in particular FPRL-1 responses.

3. Monitoring Activity of Immunomodulating Substances

To assess the activity of a possible effector the activation of different cell types from the innate immune system can be monitored.

To measure the activity of possible effectors (e.g. N-formyl methionine peptides, C-D-Methionine peptides, unmodified or modified peptides) several assays can be employed, some of them using the known receptors FPR (Formyl peptide receptor), FPLR1 (Formyl peptide like receptor) and/or FPLR2, some using whole immune cells not knowing which mechanism is important for the activation of such cells.

For example, chemotaxis and Ca(2+) mobilization are prominent read out parameters in several in vitro assays to measure the activation of dendritic cells [Yang, D. et al.; J Leukoc Biol. 2002 September; 72(3):598-607, Migeotte, I. et al; J Exp Med. 2005 January; 201(1):83-93]. Furthermore, measuring of cAMP concentrations, beta-Hexosaminidase secretion or binding assays are applicable to measure the activation of dendritic cells [Migeotte, I. et al; J Exp Med. 2005 January; 201(1):83-93; Haribabu B et al.; J Biol. Chem. 1999; 274:37087-37092]. Latter method was modified by a fluorescent cross-linking binder which binds specific to cells expressing the FPR [Mills, J S et al.; J Biol Chem 1998 April; 273(17): 10428-10435]. In this method human recombinant cells (CHO) expressing the FPR are used.

There are also different cell lines available to measure the activity of a immunomodulating substance. Cell lines such as HL-60 expressing the human N-formyl peptide receptor FPR or its two homologues (FPRL1, FPRL2) [Rabiet, M J; Eur J. Immunol. 2005 August; 35(8):2486-95] or rat basophil leukemia cell lines (FPR FPRL1) [Haribabu B et al.; J Biol. Chem. 1999; 274:37087-37092] which could trigger intracellular signalling through these receptors. Furthermore in vivo assays are described such as Air pouch experiments in mice to measure the activity of a immunomodulating substance [Chen, Q; J. Immunology. 2004; 173:2652-2659].

III. Compound Containing a Formyl Methionine Peptide as Effector and Two Peptides Binding to Hepatocellular Carcinoma Cells as Binders The peptide sequence AWYPLPP specifically recognizes and binds to hepatocellular carcinoma cells (Wei-Dong Jia et al., Cancer Lett. 2006 Jun. 24). Accordingly this peptide sequence is used as binder. The formyl methionine peptide with the sequence fMLP is used as effector.

In an analogous way as described above (I. 4.; "Branched peptides by solid phase synthesis"), a branched peptide compound is synthesized comprising the peptide sequence AWYPLPP as binder. The synthesis yields a branched conjugate of formula fMLPK-(NH2-AWYPLPP)-GGGK-(NH2-AWYPLPP)-I-COOH containing the effector fMLP-COOH and two binders NH2-AWYPLPP-COOH, wherein both, the formyl methionine of the effector as well as the N-terminus of the binder moieties are free to interact with its respective target structures.

Hepatoma cells are propagated by ip (intraperitoneal) passage in weanling strain 13 male guinea pigs (NIH). Single-cell suspensions are prepared by enzymatic digestion as described. Strain 13 male guinea pigs are injected ip with a suspension of approx. $2*10^6$ hepatoma cells to produce solid tumors (day 1). Animals are grouped into 4 groups (six animals each) and are given ip injections on day 5: Phosphate-buffered saline (PBS) (Group 1; control); 1 mg peptide NH2-AWYPLPP-COOH per animal (Group 2; binder only); 1 mg peptide fMLP-COOH per animal (Group 3; effector only); 1 mg compound fMLPK-(NH2-AWYPLPP)-GGGK-(NH2-AWYPLPP)-1-COOH per animal (Group 4). Animals are sacrificed on day 15 and tumors are excised and weighed. In addition macrophage infiltration of tumors is evaluated. Therefore, tumors are fixed in phosphate-buffered formalin and embedded in paraffin blocks. Sections (5 μm) are cut and stained for non-specific esterase activity. Esterase-positive cells are quantified with an image analyser (Optomax, Inc.).

Figure 2:
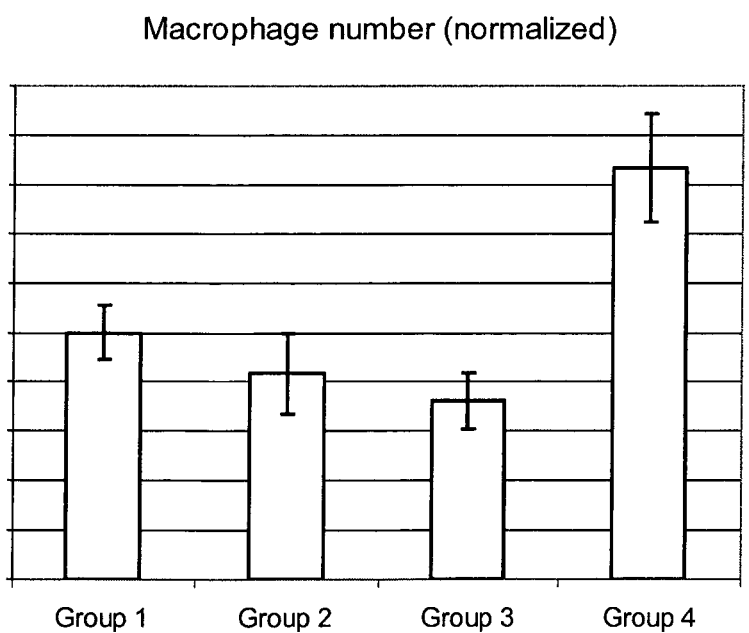
FIG. 2 shows the numbers of esterase-positive cells in tumors from guinea pigs from group 4 (injected on day 5 with compound, see Example III) are significantly increased compared to control Group 1 (PBS). Macrophages in tumors from animals from Group 2 (binder only) are comparable to Group 1. Esterase-positive cells in tumors from animals from Group 3 (effector only) are also slightly increased, but the effect is less significant than in Group 4 (compound)

Typical effects are shown in FIG. 1 and FIG. 2. The numbers of esterase-positive cells in tumors from guinea pigs from Group 4 (injected on day 5 with compound) are significantly increased, compared to control Group 1 (PBS). Macrophages in tumors from animals from Group 2 (binder only) are comparable to Group 1. Esterase-positive cells in tumors from animals from Group 3 (effector only) are also slightly increased, but the effect is less significant than in Group 4 (compound). The mean tumor weight is significantly decreased in animals from Group 4 (injected with compound) compared to control Group 1 (PBS). Groups 2 (binder only) and 3 (effector only) show no or only marginal effect on tumor size.

The present invention can allow for following advantages, especially when using synthetic structures:

Low priced and simple chemical synthesis

Simple scale up

Shorter approval times because of the chemical nature of the drugs (synthetic chemicals)

Employing standard technologies to generate binding peptides, e.g. phage display (fast, more flexible for the right combination)

Compound can be synthesized with flexible binding and effector functions and strengths (Binder)x-(Effector)y with x and y>=1

Flexibility from mono- to multivalent effector functions

Designs with several multivalent binders is possible (dendrimer or branched PEG)

No immunogenicity due to small size and pegylation

High flexibility to adapt On-/Off-rates and binding constants by screening and optimize (i) small peptides with low complexity and (ii) design scaffolds with mono- to multivalent binders Number of effectors per compound can be determined in such a way that only upon binding to a target cell the concentration of effectors will be high enough to induce immune response (a: strength of binding effector to receptor; b: multivalency)

Half-life can be varied by attaching PEG of different size, by binding to a retainer molecule and by stability Tissue penetration better due to (i) small size, (ii) influence of linkers such as PEG and (iii) hydrophilic and hydrophobic content of the peptide sequence of the binder and/or the effector moiety

TABLE 1

Examples of preferred binders

| Binder | Target molecule | Targeted cancer cell type (selection) | Targeted Tumor/Cancer Type (selection) | Affinity (kD) | Reference |
|---|---|---|---|---|---|
| CGLIIQKNEC | fibrin-fibronectin complex | | Clotted plasma at tumor-induced lesions | | Pilch et al, 2005 |
| CNAGESSKNC | fibrin-fibronectin complex | | Clotted plasma at tumor-induced lesions | | Pilch et al, 2005 |
| Dhb-pLDIK | alpha-4-beta-1 integrin (integrin receptor) | Malignant human T- and B-cell lymphomas | Non-Hodgkin's lymphoma (NHL) | | Denardo et al, 2003; Park et al, 2002 |
| Dhb-pLDI | alpha-4-beta-1 integrin (integrin receptor) | Malignant human T- and B-cell lymphomas | Non-Hodgkin's lymphoma (NHL) | | Denardo et al, 2003; Park et al, 2002 |
| WIFPWIQL | Glucose-regulated protein 78 (GRP78) | | | 5-50 nM | Arap et al, 2004 |

TABLE 1-continued

Examples of preferred binders

| Binder | Target molecule | Targeted cancer cell type (selection) | Targeted Tumor/Cancer Type (selection) | Affinity (kD) | Reference |
|---|---|---|---|---|---|
| WDLAWMFRLPVG | Glucose-regulated protein 78 (GRP78) | | | 5-50 nM | Arap et al, 2004 |
| VVISYSMPD | alpha-v-beta-5 integrin | | | | Cardo-Vila et al, 2003 |
| cyclo(RGDfK) | alpha-v-beta-3 integrin | | | 0.9 nM | Janssen et al, 2002 |
| RGDWXE | alpha-v-beta-3 integrin | | | 800 pM | Richards, 2002 |
| GGHGRVLWPDGWF SLVGISP | | CLL cells | | | Takahashi, 2003 |
| YHWYGYTPQNVI | EGFR EGFRvIII | | Colorectal Cancers | 22 nM 30 nM | Li et al 2005 Campa et al 2002 |
| TACHQHVRMVRP | | Liver Cancer Cells (BEL-7402, BEL-7404, SMMC-7721, HepG2) | | | Du et al 2006 |
| ephrin mimetic peptide | EphA2 receptor Interleukin-6 Receptor (gp80, CD126) | | | | Koolpe et al 2002 Su et al 2005 |
| NLLMAAS | Tie2 | | | | Toumaire 2004 |
| DUP-1 | | Prostate-specific membrane antigen-negative cells (DU-145) | Prostate Cancer | | Zitzmann, 2005 |
| HEWSYLAPYPWF | | Human colorectal WiDr cells | Colon Cancer | | Rasmussen, 2002 |
| HTFEPGV | | Human medullary thyroid carcinoma (MTC)-derived TT cells | Thyroid cancer | | Bockmann, 2005 |
| cyclo(SRESPHP) | | Primary orthotopically growing murine MTCs | Thyroid cancer | | Bockmann, 2005 |
| KCCYSL | Her-2 (human ErbB-2) | | Breast Cancer, Lymphoma, Pankreatic cancer, Ovarian cancer | 30 μM | Karasseva et al, 2002 |
| LTVXPWY | | SKBR3 breast cancer cells | Breast cancer | | Shadidi et al, 2003 |
| CSDSWHYWC | Human vascular endothelia growth factor receptor 3 (VEGFR-3) | | variety of human cancers | | Xin et al, 2007 |
| CSDxxHxWC | Human vascular endothelia growth factor receptor 3 (VEGFR-3) | | variety of human cancers | | Xin et al, 2007 |
| EDYELMDLLAYL | | MCF7 cells; FRO82-2 cells | follicular thyroid carcinoma; anaplastic thyroid carcinoma, mammary carcinoma, cervix carcinoma, prostate carcinoma | | Zitzmann et al, 2007 |

TABLE 1-continued

Examples of preferred binders

| Binder | Target molecule | Targeted cancer cell type (selection) | Targeted Tumor/Cancer Type (selection) | Affinity (kD) | Reference |
|---|---|---|---|---|---|
| cyclo (CVGNDNSSC) | | human tumor endothelial cells (TEC) | neoplastic vessels | | Bussolati et al, 2007 |
| TTPRDAY | | human hepatocellular carcinoma (HCC) cells | HCC | | Shimizu et al 2007 |
| VHLGYAT | | colon cancer cells (SW480; HT29) | Colon cancer | | Zhang et al, 2007 |
| CSNRDARRC | | Bladder Tumor Endothelial Cells | Bladder cancer | | Seung-Min Lee et al, 2007 |
| CXNXDXR(X)/(R)C | | Bladder Tumor Endothelial Cells | Bladder cancer | | Seung-Min Lee et al, 2007 |
| SWKLPPS | alpha3beta1 integrin | | multiple peritoneal tumors of gastric cancer | | Akita et al, 2006 |
| IAGLATPGWSHWLAL | | human PC-3 prostate carcinoma | Prostate cancer | | Newton et al, 2006 |
| AWYPLPP | novel receptor | highly metastatic human hepatocellular carcinoma (HCC) cells | HCC | | Wei-Dong Jia et al, 2006 |
| VPWMEPAYQRFL | | human neuroblastoma cells WAC 2; breast cancer cells MDA-MB-435 | Neuroblastoma; Breast cancer | 0.6 µM | Askoxylakis et al, 2006; Askoxylakis et al, 2005 |
| EPAYQR | | human neuroblastoma cells WAC 2; breast cancer cells MDA-MB-435 | Neuroblastoma; Breast cancer | | Askoxylakis et al, 2006; Askoxylakis et al, 2005 |
| KSLSRHDHIHHH | | Hepatocellular carcinoma (HCC) cells | HCC | | Yong-Qiang Jiang et al, 2006 |
| TNSLP | | colorectal tumor (carcinoma) cells | Colon cancer | | Maruta et al, 2003 |
| YYGLAEVDAGGS | | epithelial ovarian cancer cell line A2780 | Ovarian cancer | | Wang et al, 2003 |
| MQLPLAT | FGF receptor | SKOV3 cells | Ovarian cancer | 0.25 nM (if multivalent) | Maruta et al, 2002 |
| MXXP | FGF receptor | SKOV3 cells | Ovarian cancer | | Maruta et al, 2002 |

TABLE 2

Examples of target molecules

| Marker | Synonyms | Genbank Acc No | Expressed on | Cancer | Drugs approved or in development |
|---|---|---|---|---|---|
| CD20 | | | B cells | B-cell lymphomas; Non-Hodgkin's lymphoma | Rituxan ® (Mabthera ®, Rituximab); Zevalin ® (In111 + Y90-Ibritumomab); Bexxar ®(I131-Tositumomab) |

TABLE 2-continued

Examples of target molecules

| Marker | Synonyms | Genbank Acc No | Expressed on | Cancer | Drugs approved or in development |
|---|---|---|---|---|---|
| HER2 | EGFR-2; ErbB2, c-erbB2 (erbB family); Her2-neu | MI 1730 | Breast, Lung, Pankreatic, Ovarian carcinoma | 25-30% of primary Breast Cancers; Lymphomas | Herceptin ® (Trastuzumab); Pertuzumab (Omnitarg) |
| HER1 | EGFR; EGFR-1 (erbB family); ErbBI, HERI | | Colon, Head/Neck, Ovarian, Pankreatic cancer, NSCLC, breast cancer, Glioblastoma | Colorectal Cancers | Erbitux ® (Cetuximab, IgG1); Panitumomab (IgG2); Matuzumab (IgG1) |
| CD33 | | | Tumor cells, not on normal stem cells | Acute Myelogenous Leukemia (AML) | Mylotarg ® (Gemtuzumab) |
| CD22 | B-cell receptor CD22-B isoform | NP-001762.1 | B cells | B-cell Leukemias | LymphoCide |
| CD52 | | | Leukocytes; B- and T-Lymphocytes | Chronic Lymphocytic Leukemia (CLL) | MabCampath ® (Alemtuzumab) |
| HLA-DR-encoded histo-compatibility antigen | | | Lymphoma cells | Lymphoma | Oncolym ®(Lym-1) |
| Glykoprotein 17-1A | | | Adeno carcinoma of the colon | Colorectal Cancers | Panorex ® (Edrecolomab) |
| BMPRIB | bone morphogenetic protein receptor-type IB | NM-001203 | | | |
| E16 | LATI, SLC7A5 | NM-003486 | | | |
| STEAPI | Six transmembrane epithelial antigen of prostate | NM-012449 | | | |
| 0772P | CA125, MUC16 | AF361486 | | | |
| MPF | MSLN, SMR, megakaryocyte potentiating factor, mesothelin | NM-005823 | | | |
| Napi3b | NAPI-3B, NPTIIb, SLC34A2, solute carrier family 34 (sodium phosphate), member 2, type II sodium-dependent phosphate transporter 3b | NM-006424 | | | |
| Sema 5b | FLJ10372, KIAA1445, Mm. 42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B | AB040878 | | | |
| PSCA hlg | 2700050C12Rik, C530008016Rik, RIKEN cDNA 2700050C12, RIKEN cDNA 2700050C12 gene | AY358628 | | | |
| ETBR | Endothelin type B receptor | AY275463 | | | |
| MSG783 | RNF124, hypothetical protein FLJ20315 | NM~017763 | | | |
| STEAP2 | HGNC-8639, IPCA-1, PCANAP1, STAMP1, STEAP2, STMP, prostate cancer associated gene1, prostate cancer associated protein 1, six transmembrane epithelial antigen of prostate 2, six transmembrane prostate protein | AF455138 | | | |
| TrpM4 | BR22450, FLJ20041, TRPM4, TRPM4B, transient receptor potential cation channel, subfamily M, member 4 | NM~017636 | | | |
| CRIPTO | CR, CR1, CRGF, CRIPTO, TDGFI, teratocarcinoma-derived growth factor | NP~003203; NM~003212 | | | |
| CD21 | CR2 (Complement receptor 2) or C3DR (C3d/Epstein Barr virus receptor) or Hs.73792 | M26004 | | | |
| CD79b | CD79ss; IGb (immunoglobulin-associated beta), B29 | NM~000626 | | | |
| FcRH2 | IFGP4, IRTA4, SPAP1A (SH2 domain containing phosphatase anchor protein Ia), SPAP1B, SPAP1C | NM~030764 | | | |

TABLE 2-continued

Examples of target molecules

| Marker | Synonyms | Genbank Acc No | Expressed on | Cancer | Drugs approved or in development |
|---|---|---|---|---|---|
| NCA | | M18728 | | | |
| MDP | | BC017023 | | | |
| IL20Ra | | AF184971 | | | |
| Brevican | | AF229053 | | | |
| EphB2R | | NM~004442 | | | |
| ASLG659 | | AX092328 | | | |
| PSCA | | AJ297436 | | | |
| GEDA | | AY260763 | | | |
| BAFF-R | B cell-activating factor receptor, BLyS receptor 3, BR3 | NP~443177.1 | | | |
| CD79a | Immunoglobulin-associated alpha, a B cell-specific protein that covalently interacts with Ig beta (CD79B) and forms a complex on the surface with Ig M molecules, transduces a signal involved in B-cell differentiation | NP~001774.1 | B cells | | |
| CXCR5 | Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia | NP~001707.1 | | lymphoma, myeloma, and leukemia | |
| HLA-DOB | Beta subunit of MHC class II molecule (Ia antigen) that binds peptides and presents them to CD4+ T lymphocytes | NP-002111.1 | | | |
| P2X5 | Purinergic receptor P2X ligand-gated ion channel 5, an ion channel gated by extracellular ATP, may be involved in synaptic transmission and neurogenesis, deficiency may contribute to the pathophysiology of idiopathic detrusor instability | NP-002552.2 | | | |
| CD72 | B-cell differentiation antigen CD72, Lyb-2 | NP-001773.1 | | | |
| LY64 | Lymphocyte antigen 64 (RP105), type I membrane protein of the leucine rich repeat (LRR) family, regulates B-cell activation and apoptosis, loss of function is associated with increased disease activity in patients with systemic lupus erythematosis | NP-005573.1 | | | |
| FcRHI | Fc receptor-like protein 1, a putative receptor for the immunoglobulin Fc domain that contains C2 type Ig-like and ITAM domains, may have a role in B-lymphocyte differentiation | NP-443170.1 | | | |
| IRTA2 | Immunoglobulin superfamily receptor translocation associated 2, a putative immunoreceptor with possible roles in B cell development and lymphomagenesis; deregulation of the gene by translocation occurs in some B cell malignancies | NP-112571.1 | | | |
| TENB2 | putative transmembrane proteoglycan, related to the EGF/heregulin family of growth factors and follistatin | AF179274 | | | |
| Erythropoietin receptor | | | | lung cancer, non small cell lung cancers (NSCLC) | |

TABLE 2-continued

Examples of target molecules

| Marker | Synonyms | Genbank Acc No | Expressed on | Cancer | Drugs approved or in development |
|---|---|---|---|---|---|
| Thy 1.2 | CDw90; cell surface receptor; 25-35 kD transmembrane protein | | neoplastic T cells | ELA T cell lymphoma | |
| PSMA | Prostate-specific membrane antigen | | prostate epithelial cells; neovascular endothelial cells | prostate cancer | |
| LHRH Receptor | Target of LHRH (Luteinizing hormone releasing hormone) peptide | | | | |
| CEA | CD66e | | | | |
| Ep-CAM | CD326 | | | | |
| GRP78 | Glucose-regulated protein 78 | | | | |

What is claimed is:

1. A synthetic bifunctional non-antibody compound comprising one or more effector moieties and two or more binder moieties, wherein the effector moieties are operably linked to the binder moieties via a linker, the effector moieties are ligands to at least one pathogen pattern recognition receptor (PRR) and the binder moieties are peptides or peptidomimetics that bind to a marker of a tumor cell, the binder comprising any of the following peptide sequences: SEQ ID NO 2; SEQ ID NO 3; Dhb-pLDIK; Dhb-pLDI; SEQ ID NO 4; SEQ ID NO 5; SEQ ID NO 6; cyclo(RGDfK); RGDfK; SEQ ID NO 7; SEQ ID NO 8; SEQ ID NO 9; SEQ ID NO 10; SEQ ID NO 11; SEQ ID NO 12; SEQ ID NO 13; SEQ ID NO 14; SEQ ID NO 15; DUP-1; SEQ ID NO 16; SEQ ID NO 17; cyclo(SRE-SPHP); SEQ ID-NO 18; SEQ ID NO 19; SEQ ID NO 20; SEQ ID NO 21; SEQ ID NO 22; SEQ ID NO 23; cyclo (CVGNDNSSC); SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34; SEQ ID NO 35; SEQ ID NO 36; SEQ ID NO 37; MXXP, wherein X denotes any amino acid.

2. The compound of claim 1, wherein the one or more effector moieties are ligands to a mannose receptor or a formyl peptide receptor (FPR) or a member of the FPR family.

3. The compound of claim 1, wherein the one or more effector moieties is an N-formyl methionine peptide, wherein the binder moieties have the peptide sequence SEQ ID NO 31 or SEQ ID NO 37 or SEQ ID NO 38, and the one or more effector is operably linked to the binder moieties by a linker which comprises polyethylene glycol.

4. The compound of claim 1, wherein the one or more effector moieties are or contain one or more moieties selected from the group: N-formyl methionine peptide; N-formyl Met-Leu-Phe-(fMLF); N-formyl-SEQ ID NO 1; mannose; fucose; N-acetyl galactosamine; polyguanylic acid (polyG); C-terminal D-methionine.

5. The compound of claim 1, wherein the one or more effector moieties are N-formyl Met-Leu-Phe.

6. The compound of claim 1, wherein the linker is a covalent bond, an ester bond, an amide bond, a peptide bond, or an ether bond.

7. The compound of claim 1, wherein the linker is a synthetic or a semisynthetic polymer, and/or wherein the linker is comprised of an oligopeptide, of polyethylene glycol, or of polylysine.

8. A pharmaceutical composition comprising the compound according to claim 1 and a suitable carrier.

9. A synthetic bifunctional non-antibody compound comprising one or more effector moieties and two or more binder moieties, wherein the effector moieties are operably linked to the binder moieties via a linker, the effector moieties are ligands to at least one pathogen pattern recognition receptor (PRR) and the binder moieties are peptides or peptidomimetics that bind to a marker of a tumor cell, wherein the binder is SEQ ID NO 31 or SEQ ID NO 37 or SEQ ID NO 38.

* * * * *

SEQUENCE LISTING

<160> NUMBER OF SEQ ID NOS: 38

<210> SEQ ID NO 1
<211> LENGTH: 6
<212> TYPE: PRT
<213> ORGANISM: Artificial
<220> FEATURE:
<223> OTHER INFORMATION: effector peptide
<220> FEATURE:
<221> NAME/KEY: MOD_RES
<222> LOCATION: (1)..(1)
<223> OTHER INFORMATION: FORMYLATION

<400> SEQUENCE: 1

Met Met Tyr Ala Leu Phe
1               5

<210> SEQ ID NO 2
<211> LENGTH: 10
<212> TYPE: PRT
<213> ORGANISM: Artificial
<220> FEATURE:
<223> OTHER INFORMATION: binder peptide

<400> SEQUENCE: 2

Cys Gly Leu Ile Ile Gln Lys Asn Glu Cys
1               5                   10

<210> SEQ ID NO 3
<211> LENGTH: 10
<212> TYPE: PRT
<213> ORGANISM: Artificial
<220> FEATURE:
<223> OTHER INFORMATION: binder peptide

<400> SEQUENCE: 3

Cys Asn Ala Gly Glu Ser Ser Lys Asn Cys
1               5                   10

<210> SEQ ID NO 4
<211> LENGTH: 8
<212> TYPE: PRT
<213> ORGANISM: Artificial
<220> FEATURE:
<223> OTHER INFORMATION: binder peptide

<400> SEQUENCE: 4

Trp Ile Phe Pro Trp Ile Gln Leu
1               5

<210> SEQ ID NO 5
<211> LENGTH: 12
<212> TYPE: PRT
<213> ORGANISM: Artificial
<220> FEATURE:
<223> OTHER INFORMATION: binder peptide

<400> SEQUENCE: 5

Trp Asp Leu Ala Trp Met Phe Arg Leu Pro Val Gly
1               5                   10

<210> SEQ ID NO 6
<211> LENGTH: 9
<212> TYPE: PRT
<213> ORGANISM: Artificial
<220> FEATURE:
<223> OTHER INFORMATION: binder peptide

<400> SEQUENCE: 6

Val Val Ile Ser Tyr Ser Met Pro Asp
1               5

<210> SEQ ID NO 7
<211> LENGTH: 6
<212> TYPE: PRT
<213> ORGANISM: Artificial
<220> FEATURE:
<223> OTHER INFORMATION: binder peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Arg Gly Asp Trp Xaa Glu
1               5

<210> SEQ ID NO 8
<211> LENGTH: 20
<212> TYPE: PRT
<213> ORGANISM: Artificial
<220> FEATURE:
<223> OTHER INFORMATION: binder peptide

<400> SEQUENCE: 8

Gly Gly His Gly Arg Val Leu Trp Pro Asp Gly Trp Phe Ser Leu Val
1               5                   10                  15

Gly Ile Ser Pro
            20

<210> SEQ ID NO 9
<211> LENGTH: 12
<212> TYPE: PRT
<213> ORGANISM: Artificial
<220> FEATURE:
<223> OTHER INFORMATION: binder peptide

<400> SEQUENCE: 9

Tyr His Trp Tyr Gly Tyr Thr Pro Gln Asn Val Ile
1               5                   10

<210> SEQ ID NO 10
<211> LENGTH: 4
<212> TYPE: PRT
<213> ORGANISM: Artificial
<220> FEATURE:
<223> OTHER INFORMATION: binder peptide

<400> SEQUENCE: 10

Gly Tyr Thr Pro
1

<210> SEQ ID NO 11
<211> LENGTH: 6
<212> TYPE: PRT
<213> ORGANISM: Artificial
<220> FEATURE:
<223> OTHER INFORMATION: binder peptide

<400> SEQUENCE: 11

Tyr Gly Tyr Thr Pro Gln
1               5

<210> SEQ ID NO 12
<211> LENGTH: 8
<212> TYPE: PRT
<213> ORGANISM: Artificial
<220> FEATURE:
<223> OTHER INFORMATION: binder peptide

<400> SEQUENCE: 12

Trp Tyr Gly Tyr Thr Pro Gln Asn
1               5

<210> SEQ ID NO 13
<211> LENGTH: 10
<212> TYPE: PRT
<213> ORGANISM: Artificial
<220> FEATURE:
<223> OTHER INFORMATION: binder peptide

<400> SEQUENCE: 13

His Trp Tyr Gly Tyr Thr Pro Gln Asn Val
1               5                   10

<210> SEQ ID NO 14
<211> LENGTH: 12
<212> TYPE: PRT
<213> ORGANISM: Artificial
<220> FEATURE:
<223> OTHER INFORMATION: binder peptide

<400> SEQUENCE: 14

Thr Ala Cys His Gln His Val Arg Met Val Arg Pro
1               5                   10

<210> SEQ ID NO 15
<211> LENGTH: 7
<212> TYPE: PRT
<213> ORGANISM: Artificial
<220> FEATURE:
<223> OTHER INFORMATION: binder peptide

<400> SEQUENCE: 15

Asn Leu Leu Met Ala Ala Ser
1               5

<210> SEQ ID NO 16
<211> LENGTH: 12
<212> TYPE: PRT
<213> ORGANISM: Artificial
<220> FEATURE:
<223> OTHER INFORMATION: binder peptide

```
<400> SEQUENCE: 16

His Glu Trp Ser Tyr Leu Ala Pro Tyr Pro Trp Phe
1               5                   10

<210> SEQ ID NO 17
<211> LENGTH: 7
<212> TYPE: PRT
<213> ORGANISM: Artificial
<220> FEATURE:
<223> OTHER INFORMATION: binder peptide

<400> SEQUENCE: 17

His Thr Phe Glu Pro Gly Val
1               5

<210> SEQ ID NO 18
<211> LENGTH: 7
<212> TYPE: PRT
<213> ORGANISM: Artificial
<220> FEATURE:
<223> OTHER INFORMATION: binder peptide

<400> SEQUENCE: 18

Ser Arg Glu Ser Pro His Pro
1               5

<210> SEQ ID NO 19
<211> LENGTH: 6
<212> TYPE: PRT
<213> ORGANISM: Artificial
<220> FEATURE:
<223> OTHER INFORMATION: binder peptide

<400> SEQUENCE: 19

Lys Cys Cys Tyr Ser Leu
1               5

<210> SEQ ID NO 20
<211> LENGTH: 7
<212> TYPE: PRT
<213> ORGANISM: Artificial
<220> FEATURE:
<223> OTHER INFORMATION: binder peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 20

Leu Thr Val Xaa Pro Trp Tyr
1               5

<210> SEQ ID NO 21
<211> LENGTH: 9
<212> TYPE: PRT
<213> ORGANISM: Artificial
<220> FEATURE:
<223> OTHER INFORMATION: binder peptide

<400> SEQUENCE: 21

Cys Ser Asp Ser Trp His Tyr Trp Cys
1               5

<210> SEQ ID NO 22
<211> LENGTH: 9
<212> TYPE: PRT
<213> ORGANISM: Artificial
```

```
<220> FEATURE:
<223> OTHER INFORMATION: binder peptide
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Cys Ser Asp Xaa Xaa His Xaa Trp Cys
1               5

<210> SEQ ID NO 23
<211> LENGTH: 12
<212> TYPE: PRT
<213> ORGANISM: Artificial
<220> FEATURE:
<223> OTHER INFORMATION: binder peptide

<400> SEQUENCE: 23

Glu Asp Tyr Glu Leu Met Asp Leu Leu Ala Tyr Leu
1               5                   10

<210> SEQ ID NO 24
<211> LENGTH: 9
<212> TYPE: PRT
<213> ORGANISM: Artificial
<220> FEATURE:
<223> OTHER INFORMATION: binder peptide

<400> SEQUENCE: 24

Cys Val Gly Asn Asp Asn Ser Ser Cys
1               5

<210> SEQ ID NO 25
<211> LENGTH: 7
<212> TYPE: PRT
<213> ORGANISM: Artificial
<220> FEATURE:
<223> OTHER INFORMATION: binder peptide

<400> SEQUENCE: 25

Thr Thr Pro Arg Asp Ala Tyr
1               5

<210> SEQ ID NO 26
<211> LENGTH: 7
<212> TYPE: PRT
<213> ORGANISM: Artificial
<220> FEATURE:
<223> OTHER INFORMATION: binder peptide

<400> SEQUENCE: 26

Val His Leu Gly Tyr Ala Thr
1               5

<210> SEQ ID NO 27
<211> LENGTH: 9
<212> TYPE: PRT
<213> ORGANISM: Artificial
<220> FEATURE:
<223> OTHER INFORMATION: binder peptide

<400> SEQUENCE: 27

Cys Ser Asn Arg Asp Ala Arg Arg Cys
1               5
```

```
<210> SEQ ID NO 28
<211> LENGTH: 9
<212> TYPE: PRT
<213> ORGANISM: Artificial
<220> FEATURE:
<223> OTHER INFORMATION: binder peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
      or arginine

<400> SEQUENCE: 28

Cys Xaa Asn Xaa Asp Xaa Arg Xaa Cys
1               5

<210> SEQ ID NO 29
<211> LENGTH: 7
<212> TYPE: PRT
<213> ORGANISM: Artificial
<220> FEATURE:
<223> OTHER INFORMATION: binder peptide

<400> SEQUENCE: 29

Ser Trp Lys Leu Pro Pro Ser
1               5

<210> SEQ ID NO 30
<211> LENGTH: 15
<212> TYPE: PRT
<213> ORGANISM: Artificial
<220> FEATURE:
<223> OTHER INFORMATION: binder peptide

<400> SEQUENCE: 30

Ile Ala Gly Leu Ala Thr Pro Gly Trp Ser His Trp Leu Ala Leu
1               5                   10                  15

<210> SEQ ID NO 31
<211> LENGTH: 7
<212> TYPE: PRT
<213> ORGANISM: Artificial
<220> FEATURE:
<223> OTHER INFORMATION: binder peptide

<400> SEQUENCE: 31

Ala Trp Tyr Pro Leu Pro Pro
1               5

<210> SEQ ID NO 32
<211> LENGTH: 12
<212> TYPE: PRT
<213> ORGANISM: Artificial
<220> FEATURE:
<223> OTHER INFORMATION: binder peptide
```

```
<400> SEQUENCE: 32

Val Pro Trp Met Glu Pro Ala Tyr Gln Arg Phe Leu
1               5                   10

<210> SEQ ID NO 33
<211> LENGTH: 6
<212> TYPE: PRT
<213> ORGANISM: Artificial
<220> FEATURE:
<223> OTHER INFORMATION: binder peptide

<400> SEQUENCE: 33

Glu Pro Ala Tyr Gln Arg
1               5

<210> SEQ ID NO 34
<211> LENGTH: 12
<212> TYPE: PRT
<213> ORGANISM: Artificial
<220> FEATURE:
<223> OTHER INFORMATION: binder peptide

<400> SEQUENCE: 34

Lys Ser Leu Ser Arg His Asp His Ile His His His
1               5                   10

<210> SEQ ID NO 35
<211> LENGTH: 5
<212> TYPE: PRT
<213> ORGANISM: Artificial
<220> FEATURE:
<223> OTHER INFORMATION: binder peptide

<400> SEQUENCE: 35

Thr Asn Ser Leu Pro
1               5

<210> SEQ ID NO 36
<211> LENGTH: 12
<212> TYPE: PRT
<213> ORGANISM: Artificial
<220> FEATURE:
<223> OTHER INFORMATION: binder peptide

<400> SEQUENCE: 36

Tyr Tyr Gly Leu Ala Glu Val Asp Ala Gly Gly Ser
1               5                   10

<210> SEQ ID NO 37
<211> LENGTH: 7
<212> TYPE: PRT
<213> ORGANISM: Artificial
<220> FEATURE:
<223> OTHER INFORMATION: binder peptide

<400> SEQUENCE: 37

Met Gln Leu Pro Leu Ala Thr
1               5

<210> SEQ ID NO 38
<211> LENGTH: 13
<212> TYPE: PRT
<213> ORGANISM: Artificial
<220> FEATURE:
<223> OTHER INFORMATION: binder peptide
```

-continued

```
<400> SEQUENCE: 38

Tyr His Trp Tyr Gly Tyr Thr Pro Gln Asn Val Ile Lys
1               5                   10
```